United States Patent
Sim et al.

(10) Patent No.: US 9,422,307 B2
(45) Date of Patent: Aug. 23, 2016

(54) 2,4,7-SUBSTITUTED THIENO[3,2-D]PYRIMIDINE COMPOUNDS AS PROTEIN KINASE INHIBITORS

(75) Inventors: Tae Bo Sim, Seoul (KR); Jung Mi Hah, Seoul (KR); Hwan Geun Choi, Seoul (KR); Young Jin Ham, Seoul (KR); Jung Hun Lee, Busan (KR); Dong Sik Park, Busan (KR); Hwan Kim, Goyang-si (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 598 days.

(21) Appl. No.: 13/510,743

(22) PCT Filed: Oct. 22, 2010

(86) PCT No.: PCT/KR2010/007275
§ 371 (c)(1),
(2), (4) Date: Sep. 17, 2012

(87) PCT Pub. No.: WO2011/062372
PCT Pub. Date: May 26, 2011

(65) Prior Publication Data
US 2013/0012703 A1 Jan. 10, 2013

(30) Foreign Application Priority Data
Nov. 19, 2009 (KR) .................. 10-2009-0112132

(51) Int. Cl.
C07D 495/04 (2006.01)
A61K 31/519 (2006.01)
A61P 35/04 (2006.01)

(52) U.S. Cl.
CPC .................. *C07D 495/04* (2013.01)

(58) Field of Classification Search
CPC ..................... C07D 495/04; A61K 31/519
USPC ....................... 544/278; 514/260.1
See application file for complete search history.

(56) References Cited

U.S. PATENT DOCUMENTS

2011/0130849 A1 6/2011 Kim et al.

OTHER PUBLICATIONS

G. Manning et al., "The Protein Kinase Complement of the Human Genome", Science, vol. 298, Dec. 2002, pp. 1912-1934.
Elizabeth A. Beierle et al., "TAE226 Inhibits Human Neuroblastoma Cell Survival", Cancer Investigations, vol. 26, 2008, pp. 145-151.
Jyotsnabaran Halder et al., "Therapeutic Efficacy of a Novel Focal Adhesion Kinase Inhibitor TAE226 in Ovarian Carcinoma", Cancer Research, vol. 67, Nov. 2007, pp. 10976-10983.
Jill K. Slack-Davis et al., "Cellular characterization of FAK family kinase inhibitors", Cellular and Molecular Biology, vol. 69, abstract only, (2006).
S. Roelle et al., "Essential role of Pyk2 and Src kinase activation in neuropeptide-induced proliferation of small cell lung cancer cells", Oncogene, vol. 27, 2008, pp. 1737-1748.
T-C Yuan et al., "ErbB-2 via PYK2 upregulates the adhesive ability of androgen receptor-positive human prostate cancer cells", Oncogene, vol. 26, 2007, pp. 7552-7559.
CK Sun et al., "The significance of proline-rich tyrosine kinase2 (Pyk2) on hepatocellular carcinoma progression and recurrence", British Journal of Cancer, vol. 97, 2007, pp. 50-57.
Christopher A. Lipinski et al., "The Tyrosine Kinase Pyk2 Promotes Migration and Invasion of Glioma Cells", Neolasia, vol. 7, No. 5, May 2005, pp. 435-445.
Michael S. Lyons, et al., "Isolation of the Zebrafish Homologues for the *tie-1* and *tie-2* Endothelium-Specific Receptor Tyrosine Kinases", Developmental Dynamics, vol. 212, 1998, pp. 133-140.
KG Peters et al., "Expression of Tie2/Tek in breast tumor vasculature provides a new marker for evaluation of tumor angiogenesis", British Journal of Cancer, vol. 77, No. 1, 1998, pp. 51-56.
Nina Jones et al., "Identification of Tek/Tie2 Binding Partners", The Journal of Biological Chemistry, vol. 274, No. 43, Oct. 1999, pp. 30896-30905.
International Preliminary Report on Patentability mailed May 31, 2012, issued in corresponding PCT Patent Application No. PCT/KR2010/007275.

*Primary Examiner* — Susanna Moore
(74) *Attorney, Agent, or Firm* — Goldilocks Zone IP Law

(57) ABSTRACT

A substituted thieno pyrimidine compound of Formula 1, pharmaceutically acceptable salts and a pharmaceutical composition thereof is provided.

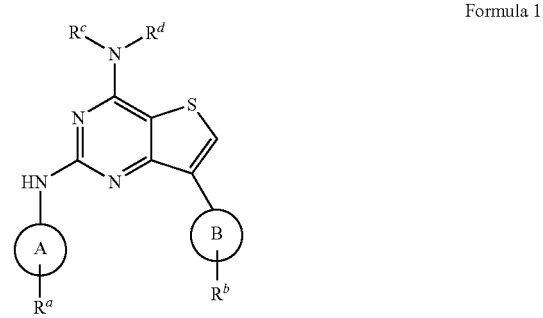

Formula 1

The compound of Formula 1 exhibits superior inhibition activity against various protein kinases involved in growth factor signal transduction. The compound of Formula 1 and its compositions are useful for the prevention and treatment of diseases caused by abnormal cell growth including cancer.

12 Claims, No Drawings

2,4,7-SUBSTITUTED THIENO[3,2-D]PYRIMIDINE COMPOUNDS AS PROTEIN KINASE INHIBITORS

CROSS REFERENCE TO RELATED APPLICATIONS

This application claims the benefit of International Application No. PCT/KR2010/007275, filed Oct. 22, 2010, and claims the benefit of Korean Application No. 10-2009-0112132, filed Nov. 19, 2009, the disclosures of all of which are incorporated herein by reference.

TECHNICAL FIELD

The present invention relates to a 2,4,7-substituted thieno [3,2-d]pyrimidine compound having a protein kinase inhibition activity, a pharmaceutically acceptable salt, and a pharmaceutical composition for prevention and treatment of diseases caused by abnormal cell growth including the compound as an effective ingredient.

BACKGROUND ART

A protein kinase is an enzyme which catalyzes phosphorylation of hydroxyl groups on tyrosine, serine and threonine residues of proteins. It plays an important role in signal transduction of growth factors involved in growth, differentiation and proliferation of cells.

To maintain homeostasis, it is necessary to keep good balance in turning on and off of the signal transduction system. However, mutation or overexpression of specific protein kinases disrupts the signal transduction system in normal cells and causes various diseases including cancers, inflammations, metabolic diseases, brain diseases, etc. Examples of the typical protein kinases that lead to diseases caused by abnormal cell growth are Raf, KDR, Fms, Tie2, SAPK2a, Ret, Abl, Abl (T315I), ALK, Aurora A, Bmx, CDK/cyclinE, Kit, Src, EGFR, EphA1, FGFR3, Flt3, Fms, IGF-1R, IKKb, IR, Itk, JAK2, KDR, Met, mTOR, PDGFRa, Plk1, Ret, Syk, Tie2, TrtB, etc.

It is estimated that there are 518 different kinds of protein kinase genes in humans constituting about 1.7% of the entire human genes [Manning et al., *Science*, 2002, 298, 1912]. Human protein kinases are largely divided into tyrosine-specific protein kinases and serine/threonine-specific protein kinase. The tyrosine-specific protein kinases may be divided into 58 receptor tyrosine kinases, which are grouped into 20 subfamilies, and 32 cytoplasmic/non-receptor tyrosine kinases, which are grouped into 10 subfamilies. The receptor tyrosine kinase has an extracellular domain capable of binding to a growth factor and a cytoplasmic active site that can phosphorylate the tyrosine residue. When a growth factor binds to the extracellular growth factor receptor site of the receptor tyrosine kinase, the receptor tyrosine kinase forms a dimer and the tyrosine residues in cytoplasm are autophosphorylated. Then, the downstream proteins are sequentially phosphorylated, and as the signal transduction proceeds in the nucleus, the transcription factors that induce cancer are overexpressed in the end.

Focal adhesion kinase (FAK) is a 125 kD tyrosine-specific protein kinase present in cytoplasm. FAK plays a critical role in migration, proliferation and survival of cells by regulating the signal transduction system of integrin and growth factors. FAK protein and FAK mRNA were found to be overexpressed/activated in various cancer cells, including squamous cell carcinoma, invasive rectal cancer/breast cancer, metastatic prostate cancer, melanoma and glioma. Novartis' FAK inhibitor TAE226 [*Cancer Invest.* 2008, 26(2), 145] was shown effective for the treatment of breast cancer through three different kinds of animal models (HeyA8, SKOV3ip1 and HeyA8-MDR) [*Cancer Res.* 2007, 67(22), 10976)]. Further, Pfizer's FAK inhibitor PF-573,228 [*Proc. Am. Assoc. Cancer Res.*, 2006, 47, Abst. 5072] is under successful clinical trial. It was shown effective for the treatment of prostate cancer (PC-3M), breast cancer (BT474), pancreatic cancer (BxPc3), lung cancer (H460) and brain cancer (U87MG) in animal models. In addition, a concurrent administration of FAK inhibitor (TAE226) and docetaxel showed an excellent efficiency (85-97% tumor reduction, P values<0.01) in an animal model [*Cancer Res.* 2007, 67(22), 10976].

FAK is involved in the signaling of integrin. When integrin receptors duster in response to various stimulations from outside, the cytoplasmic domain (cytoplasmic tail) of integrin binds to the cytoskeleton and signaling proteins. The FERM (F for 4.1 protein, E for ezrin, R for radixin and M for moesin) domain and the focal adhesion targeting (FAT) domain of FAK independently bind to the cytoplasmic domain of integrin and allow the FAK to be located at the focal adhesion site. The FAKs clustered close to the focal adhesion site are activated via intramolecular or intermolecular phosphorylation of the Y397 residue. Then, the SH2 domain of Src kinase binds to the phosphorylated Y397 residue of FAK to form an FAK/Src complex. The Src kinase bound to FAK further phosphorylates other tyrosine residues (Y407, Y576/577, Y861 and Y925) of FAK. Also, the FAK/Src complex binds to various signaling proteins (P130Cas, Grb2, PI3K and Grb7) and mediates phosphorylation. In normal cells, the signal transduction through FAK is mediated under strict regulation. However, in tumorized cells, FAK is overexpressed and activated thereby exhibiting various features of malignant tumors. FAK facilitates proliferation of cancer cells, increases invasion, and migration of cancer cells. Further, FAK is also known to suppress cancer cell apoptosis and increase angiogenesis.

FAK is a protein targeted by many growth factor receptors including epidermal growth factor receptor (EGFR) and platelet-derived growth factor receptor (PDGFR), as well as integrin. Overexpression of the receptors or expression of activated receptors converts normal cells into tumor cells. Thus, FAK is an important kinase involved in tumor-related signal transduction of the receptors. It has been reported that the N-terminal FERM domain of FAK binds to EGFR and the C-terminal domain of FAK is involved in the cell migration mediated by epidermal growth factor (EGF). That is, FAK recognizes the signal from the EGFR receptor through the N-terminal FERM domain and recognizes the signal from the integrin through the C-terminal FAT domain, thereby integrating signals from the outside of the cell.

Apoptosis may be induced by inhibiting FAK in various manners. Cell survival mediated by FAK is mainly conducted by phosphoinositide 3-kinase (PI 3-kinase). The phosphorylated Y397 site of FAK binds to PI 3-kinase and synthesizes PI(3,4,5)P3 and PI(3,4)P2 as second messengers, which move protein kinase B (PKB, also called AKT) to the cell membrane so that it can be phosphorylated by 3'-phosphoinositide-dependent kinase (PDK). Thus activated PKB deactivates apoptotic proteins (e.g., p21WAF, FKHR, Bad and GSK-3), and thereby inhibits apoptosis. Another signal for survival is the binding of the SH3 domain of p130Cas to the proline-rich motif of FAK, whereby phosphorylation of the tyrosine residues of p130Cas is induced by FAK/Src and Ras is activated.

The role of FAK in the cell cycle is explained as follows. If the Y925 site is phosphorylated, FAK binds to growth factor receptor-bound protein 2 (Grb2) thereby activating the Ras/Erk pathway. Overexpression of FAK facilitates G1 to S phase transition, and expression of FAK related non-kinase (FRNK), an inhibitor of FAK, inhibits the expression of cyclin D1 and induces the expression of the CDK inhibitor p21, thereby delaying the progress of the cell cycle. However, overexpression of cyclin D1 rescues the cells from the cell cycle arrest by FRNK.

The only subtype of FAK, proline-rich tyrosine kinase 2 (PYK2), is the most highly distributed in nerve cells. Recently, it was reported as a useful molecular target in the development of anticancer drugs for small-cell lung cancer [*Oncogene*. 2008, 27(12), 1737], prostate cancer [*Oncogene*. 2007, 26(54), 7552], liver cell carcinoma [*Br. J. Cancer*. 2007, 97(1), 50] and glioma [*Neoplasia*. 2005, 7(5), 435].

FAK comprises four domains: 1) The FERM (band 4.1 protein, ezrin, radixin, moesin) domain is an amino-terminal domain that interacts with integrin receptor, platelet-derived growth factor receptor (PDGFR), epidermal growth factor receptor (EGFR), etc. and inhibits kinase activity through direct interaction with the kinase domain; 2) the kinase domain; 3) three proline-rich (PR) regions; and 4) the focal adhesion targeting (FAT) domain positioned at the carboxyl-terminal interacts with paxillin, talin, p190RhoGEF, RhoA-specific GDP/GTP exchange factor, etc. The alternative splicing product of FAK, FAK-related non-kinase domain (FRNK), consists of PR1, PR2 and FAT domains and acts as an antagonistic regulatory factor of FAK.

For the activation of FAK, it is essential to have autophosphorylation of Y397 located at the junction of the FERM and kinase domains. Src kinase binds to the phosphorylated Y397 and sequentially phosphorylates Y576 and 577. When Y925 is phosphorylated in the end, the signal transduction of FAK is turned on through Grb2. The FAK inhibitors currently under development are shown to inhibit the autophosphorylation of Y397 by targeting the ATP binding site of the kinase domain. The extent of the inhibition of Y397 autophosphorylation is an important biomarker in the efficiency test using an animal model.

The progress that has been made in the development of low molecular weight FAK inhibitors is as follows. Of the 26 lead compounds that have been proposed for the FAK inhibitors, only the Pfizer's PF-562271 is under clinical trial phase I at present. PF-562271 is an ATP-competitive FAK inhibitor ($IC_{50}$=1.5 nM) and a homologous Pyk2 inhibitor (13 nM). It inhibits autophosphorylation at the FAK Y397 site in fibroblasts, epithelial cells and cancer cells. Further, it inhibits the migration of most cancer cells, but does not affect the growth of normal cells. No special toxicity has been observed and inhibition of tumor growth or tumor degeneration by 42-90% was observed in in vivo human tumor xenograft tests (25-100 mg/kg p.o.) for prostate cancer PC-3, breast cancer BT-474, colon LoVo, lung cancer NCI-H460, glioblastoma U-87 MG and pancreatic cancer BxPC-3 cells.

Vascular endothelial growth factor receptors (VEGFRs) are receptor tyrosine kinases (RTKs) and important regulatory factors of angiogenesis. They are involved in the formation of blood vessels and lymphatic vessels and in homeostasis, and exert important effects on nerve cell. Vascular endothelial growth factor (VEGF) is produced mostly by vascular endothelial cells, hematopoietic cells and stromal cells under a hypoxic condition or by stimulations from growth factors such as TGF, interleukin and PDGF. VEGF binds to VEGFR-1, -2 and -3. Each VEGF isoform binds to a specific receptor, thereby inducing the formation of a receptor homozygote or heterozygote, and activates each signal transduction system. The signal specificity of VEGFR is further fine-tuned by co-receptors such as neuropilin, heparan sulfate, integrin, cadherin, or the like.

The biological function of VEGF is mediated by type III RTK, VEGFR-1 (Flt-1), VEGFR-2 (KDR/Flk-1) and VEGFR-3 (Flt-4). VEGFR is closely related to Fms, Kit and PDGFR. Each VEGF binds to specific receptors. VEGF-A binds to VEGFR-1, -2 and receptor zygote, whereas VEGF-C binds to VEGF-2, -3. PIGF and VEGF-B interact exclusively with VEGFR-1, and VEGF-E interacts only with VEGFR-2. VEGF-F interacts with VEGFR-1 or -2. Whereas VEGF-A, -B and PIGF are preferentially required for the formation of blood vessels, VEGF-C and -D are essential in the formation of lymphatic vessels. Angiogenesis is essential in the proliferation and transition of tumors, since it supplies nutrients and oxygen to the tumors and provides channels for transition to cancer cells. Normally, angiogenesis is balanced by angiogenesis promoters and angiogenesis inhibitors. If the balance is broken, as in cancer cells, the growth factor that affects the vascular endothelial cells most, i.e., VEGF, activates its receptor, VEGFR. At present, various researches are under way on the inhibitors that inhibit the receptor tyrosine kinase of VEGF using low molecular weight synthetic substances, which are advantageous in that they are applicable also to solid tumors and have fewer side effects because they inhibit angiogenesis in the cancer cells only.

Tie2 is a kind of receptor tyrosine kinase and is deeply involved with angiogenesis and vasculature. The domain structure of Tie2 is very highly conserved in all vertebrates [Lyons et al., 1998]. The ligand of Tie2 is angiopoietin (Ang). Ang2 does not induce autophosphorylation of Tie2, but interferes with the activation of Tie2 by Ang1. In endothelial cells, the activation of Tie2 by Ang2 induces activation of PI3K-Akt [Jones et al., 1999]. In the mitogen-activated protein kinase (MAPK) signal transduction pathway, which is the main signal transduction system of Tie2, the adaptor protein GRB2 and the protein tyrosine phosphatase SHP2 play a key role in dimerization of the Tie2 receptor tyrosine kinase through autophosphorylation. Ang/Tie2 and the VEGF signal transduction pathway are important in angiogenesis of cancer cells. Tie2 is expressed in vascular endothelial cells. Especially, the expression increases remarkably at the site invaded by cancer cell. Overexpression of Tie2 was observed in breast cancer [Peters et al., 1998] and also in uterine cancer, liver cancer and brain cancer.

Several compounds with the thieno[3,2-d]pyrimidine structure have been synthesized. However, the substituted thieno[3,2-d]pyrimidine compound of the present invention with specific substituents at the 2-, 4- and 7-positions of thieno[3,2-d]pyrimidine is a novel compound not disclosed in any literature. Moreover, the inhibition activity against various protein kinases or the possibility of the substituted thieno[3,2-d]pyrimidine compound with the specific substituents at the 2-, 4- and 7-positions has not been predicted in any literature.

DISCLOSURE

Technical Problem

An object of the present invention is to provide a novel 2,4,7-substituted thieno[3,2-d]pyrimidine compound having specific substituents at the 2-, 4- and 7-positions of thieno[3,2-d]pyrimidine or a pharmaceutically acceptable salt.

Another object of the present invention is to provide a pharmaceutical composition for prevention and treatment of cancers caused by abnormal cell growth comprising the novel 2,4,7-substituted thieno[3,2-d]pyrimidine compound or a pharmaceutically acceptable salt as an effective ingredient.

Technical Solution

The present invention provides a 2,4,7-substituted thieno[3,2-d]pyrimidine compound represented by Chemical Formula 1, an isomer thereof, a pharmaceutically acceptable salt thereof, a hydrate thereof or a solvate thereof:

[Chemical Formula 1]

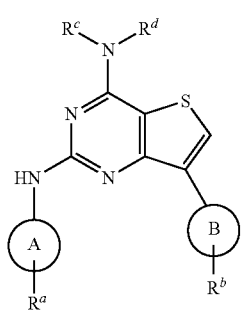

wherein

A represents hydroxy$C_1$-$C_6$ alkyl, morpholino$C_1$-$C_6$ alkyl, phenyl, or 5- to 14-membered single or fused heteroaryl containing 1 to 3 nitrogen atom(s);

$R^a$ represents hydrogen, $C_1$-$C_6$ alkyl, $C_1$-$C_6$ alkoxy, or 5- to 7-membered heterocycloalkyl containing 1 to 3 heteroatom(s) selected from oxygen and nitrogen atoms;

B represents $C_1$-$C_6$ alkyl, $C_2$-$C_6$ alkenyl, $C_2$-$C_6$ alkynyl, phenyl, or 5- to 14-membered single or fused heteroaryl containing 1 to 3 nitrogen atom(s);

$R^b$ represents hydrogen, —C(O)$NR^1R^2$, —$NR^3$C(O)$R^1$, —$NR^2$C(O)$NR^1R^2$, —$SO_2NR^1R^2$ or —$NR^3SO_2R^1$;

$R^c$ and $R^d$, which are the same or different, represent hydrogen, $C_1$-$C_6$ alkyl or —$(CH_2)_n$-phenyl;

$R^1$ and $R^2$, which are the same or different, represent hydrogen, $C_1$-$C_6$ alkyl, $C_1$-$C_6$ haloalkyl, —$(CH_2)_n$-phenyl, or 5- to 12-membered single or fused heteroaryl containing 1 to 4 heteroatom(s) selected from oxygen, nitrogen and sulfur atoms;

$R^3$ represents hydrogen or $C_1$-$C_6$ alkyl;

n represents an integer from 0 to 6; and each of the phenyl, heterocycloalkyl and heteroaryl is substituted or unsubstituted with a substituent selected from halo, hydroxy, amino, $C_1$-$C_6$ haloalkyl, $C_1$-$C_6$ alkyl, $C_1$-$C_6$ alkoxy, $C_1$-$C_6$ alkylamino, di($C_1$-$C_6$ alkyl)amino and pyrrolidinyl.

Advantageous Effects

The 2,4,7-substituted thieno[3,2-d]pyrimidine compound represented by Chemical Formula 1, an isomer thereof, a pharmaceutically acceptable salt thereof, a hydrate thereof or a solvate thereof has superior capability of inhibiting the activity of protein kinases selected from ALK, Abl, CDK, Aurora, EphA1, FAK, Flt3, Fms, Itk, KDR, Kit, Met, Ret, Raf, Src, Syk, Tie2 and TrkB, and is effective for preventing and treating cancers caused by abnormal cell growth.

Specifically, the cancers caused by abnormal cell growth that may be prevented or treated by the compound according to the present invention may include various cancers selected from stomach cancer, lung cancer, liver cancer, colorectal cancer, small intestine cancer, pancreatic cancer, brain cancer, bone cancer, melanoma, breast cancer, sclerosing adenoma, uterine cancer, cervical cancer, head and neck cancer, esophageal cancer, thyroid cancer, parathyroid cancer, renal cancer, sarcoma, prostate cancer, urethral cancer, bladder cancer, leukemia, multiple myeloma, hematological malignancy such as myelodysplastic syndrome, lymphoma such as Hodgkin's disease and non-Hodgkin lymphoma, fibroadenoma, or the like.

BEST MODE

Hereinafter, the embodiments of the present invention will be described in detail.

The 2,4,7-substituted thieno[3,2-d]pyrimidine compound represented by Chemical Formula 1 may have one or more chiral center(s), and, in that case, the compound may exist as enantiomers or diastereomers. In case the compound represented by Chemical Formula 1 has an alkenyl or alkynyl group, it may exist as cis or trans isomers. Accordingly, the present invention includes the isomers of the compound represented by Chemical Formula 1 or a mixture of the isomers.

Further, the 2,4,7-substituted thieno[3,2-d]pyrimidine compound represented by Chemical Formula 1 may exist as a pharmaceutically acceptable salt. The pharmaceutically acceptable salt should be less toxic to the human body and should not have negative effects on the biological activity and physical and chemical properties of the mother compound, and may be prepared according to a method commonly employed in the art. The pharmaceutically acceptable salt includes a free acid, an acid addition salt of a base compound represented by Chemical Formula 1, an alkali metal salt (e.g., a sodium salt), an alkaline earth metal salt (e.g., a calcium salt), an organic salt, an organic base addition salt of a carboxylic acid represented by Chemical Formula 1, and an amino acid addition salt. The free acid that may be used to prepare the pharmaceutically acceptable salt includes an inorganic acid or an organic acid. The inorganic acid may be hydrochloric acid, sulfuric acid, nitric acid, phosphoric acid, perchloric acid, bromic acid, or the like. The organic acid may be acetic acid, methanesulfonic acid, ethanesulfonic acid, p-toluenesulfonic acid, fumaric acid, maleic acid, malonic acid, phthalic acid, succinic acid, lactic acid, citric acid, gluconic acid, tartaric acid, salicylic acid, malic acid, oxalic acid, benzoic acid, embonic acid, aspartic acid, glutamic acid, or the like. The organic base that may be used to prepare the organic base addition salt includes tris(hydroxymethyl)methylamine, dicyclohexylamine, or the like. The amino acid that may be used to prepare the amino acid addition salt includes a naturally occurring amino acid such as alanine, glycine, or the like.

The 2,4,7-substituted thieno[3,2-d]pyrimidine compound represented by Chemical Formula 1 includes, in addition to the pharmaceutically acceptable salts, all hydrates and solvates. The hydrate or the solvate may be prepared by dissolving the 2,4,7-substituted thieno[3,2-d]pyrimidine compound represented by Chemical Formula 1 in a water-miscible solvent such as methanol, ethanol, acetone or 1,4-dioxane, adding a free acid or a free base thereto, and then performing crystallization or recrystallization. Accordingly, the compound of the present invention includes, in addition to the compounds containing various amounts of water that can be prepared through, for example, lyophilization, stoichiometric solvates including hydrates.

Hereunder is given a detailed description about the substituents used to define the compound according to the present invention.

In the present invention, 'halogen atom' means a fluorine, chlorine, bromine or iodine atom.

In the present invention, 'alkyl' means a $C_1$-$C_6$ aliphatic saturated hydrocarbon group, including methyl, ethyl, n-propyl, i-propyl, cyclopropyl, n-butyl, i-butyl, t-butyl, cyclobutyl, cyclopropylmethyl, n-pentyl, i-pentyl, neopentyl, t-pentyl, cyclopentyl, cyclobutylmethyl, n-hexyl, i-hexyl, cyclohexyl, cyclopentylmethyl, or the like.

In the present invention, 'haloalkyl' means an alkyl group with one or more hydrogen(s) substituted by halogen atom(s), such as trifluoromethyl.

In the present invention, 'alkoxy' means a hydroxyl group with the hydrogen substituted by a $C_1$-$C_{10}$ alkyl group substituent, such as methoxy, ethoxy, n-propoxy, i-propoxy, n-butoxy, i-butoxy and t-butoxy.

In the present invention, 'heteroaryl' means a mono-, bi- or tricyclic aromatic heterohydrocarbon group containing one or more heteroatom(s) selected from oxygen, nitrogen and sulfur atoms, such as pyrrolyl, furanyl, thiophenyl, pyrazolyl, imidazolyl, oxazolyl, isoxazolyl, thiazolyl, isothiazolyl, triazolyl, oxadiazolyl, thiadiazolyl, tetrazolyl, pyridinyl, pyrazinyl, pyridazinyl, pyrimidinyl, triazolyl, indolyl, isoindolyl, benzofuranyl, benzofurazanyl, dibenzofuranyl, isobenzofuranyl, indazolyl, benzimidazolyl, benzoxazolyl, benzisoxazolyl, benzo[d]thiazolyl, dibenzothiophenyl, naphthyridyl, benzisothiazolyl, quinolinyl, isoquinolinyl, quinoxalinyl, phthalazinyl, phthalazinyl, quinazolinyl, or the like.

In the present invention, 'heterocycloalkyl' means a 5- to 7-membered heterohydrocarbon group containing one or more heteroatom(s), such as morpholinyl, piperidinyl, piperazinyl, N-protected piperazinyl, or the like.

Preferably, in the 2,4,7-substituted thieno[3,2-d]pyrimidine compound represented by Chemical Formula 1, A represents hydroxy$C_1$-$C_6$ alkyl, morpholino$C_1$-$C_6$ alkyl, phenyl, pyridinyl or pyrimidinyl; $R^a$ represents hydrogen, $C_1$-$C_6$ alkyl, $C_1$-$C_6$ alkoxy, morpholino, piperidinyl substituted or unsubstituted with a substituent selected from hydroxy, $C_1$-$C_6$ alkyl, amino, $C_1$-$C_6$ alkylamino, di($C_1$-$C_6$ alkyl)amino and pyrrolidinyl, or piperazinyl substituted or unsubstituted with a substituent selected from hydroxy and $C_1$-$C_6$ alkyl; B represents $C_1$-$C_6$ alkyl, $C_2$-$C_6$ alkenyl, $C_2$-$C_6$ alkynyl, phenyl or quinolinyl; $R^b$ represents hydrogen, —C(O)NR$^1$R$^2$, —NR$^3$C(O)R$^1$, —NR$^2$C(O)NR$^1$R$^2$, —SO$_2$NR$^1$R$^2$ or —NR$^3$SO$_2$R$^1$; $R^c$ and $R^d$, which are the same or different, represent hydrogen, $C_1$-$C_6$ alkyl or —(CH$_2$)$_n$-phenyl; R$^1$ and R$^2$, which are the same or different, represent hydrogen, $C_1$-$C_6$ alkyl, $C_1$-$C_6$ haloalkyl, —(CH$_2$)$_n$-phenyl, or 5- to 12-membered single or fused heteroaryl containing 1 to 4 heteroatom(s) selected from oxygen, nitrogen and sulfur atoms, wherein the phenyl or the heteroaryl is substituted or unsubstituted with a substituent selected from halo, $C_1$-$C_6$ haloalkyl, $C_1$-$C_6$ alkyl and $C_1$-$C_6$ alkoxy; R$^3$ represents hydrogen or $C_1$-$C_6$ alkyl; and n represents an integer from 0 to 3.

Specific examples of the 2,4,7-substituted thieno[3,2-d]pyrimidine compound represented by Chemical Formula 1 include:

3-(4-amino-2-(6-(4-ethylpiperazin-1-yl)pyridin-3-ylamino)thieno[3,2-d]pyrimidin-7-yl)-N-methylbenzamide;

3-(4-amino-2-(6-morpholinopyridin-3-ylamino)thieno[3,2-d]pyrimidin-7-yl)-N-methylbenzamide;

3-(4-amino-2-(4-(4-hydroxypiperidin-1-yl)phenylamino)thieno[3,2-d]pyrimidin-7-yl)-N-methylbenzamide;

3-(4-amino-2-(4-(1-ethylpiperidin-4-yl)phenylamino)thieno[3,2-d]pyrimidin-7-yl)-N-methylbenzamide;

3-(4-amino-2-(3-(4-ethylpiperazin-1-yl)phenylamino)thieno[3,2-d]pyrimidin-7-yl)-N-methylbenzamide;

3-(4-amino-2-(4-(4-ethylpiperazin-1-yl)phenylamino)thieno[3,2-d]pyrimidin-7-yl)-N-methylbenzamide;

3-(4-amino-2-(4-(4-(pyrrolidin-1-yl)piperidin-1-yl)phenylamino)thieno[3,2-d]pyrimidin-7-yl)-N-methylbenzamide;

3-(4-amino-2-(6-morpholinopyrimidin-4-ylamino)thieno[3,2-d]pyrimidin-7-yl)-N-methylbenzamide;

3-(4-amino-2-(6-(4-ethylpiperazin-1-yl)pyrimidin-4-ylamino)thieno[3,2-d]pyrimidin-7-yl)-N-methylbenzamide;

3-(4-amino-2-(2-methoxy-4-morpholinophenylamino)thieno[3,2-d]pyrimidin-7-yl)-N-methylbenzamide;

7-(3-aminophenyl)-N$^2$-(3,4,5-trimethoxyphenyl)thieno[3,2-d]pyrimidin-2,4-diamine;

1-(3-(4-amino-2-(3,4,5-trimethoxyphenylamino)thieno[3,2-d]pyrimidin-7-yl)phenyl)-3-isopropylurea;

N-(3-(4-amino-2-(3,4,5-trimethoxyphenylamino)thieno[3,2-d]pyrimidin-7-yl)phenyl)methanesulfonamide;

1-(3-(4-amino-2-(3,4,5-trimethoxyphenylamino)thieno[3,2-d]pyrimidin-7-yl)phenyl)-3-(4-chloro-3-(trifluoromethyl)phenyl)urea;

N-(3-(4-amino-2-(3,4,5-trimethoxyphenylamino)thieno[3,2-d]pyrimidin-7-yl)phenyl)cyclopropanecarboxamide;

N-(3-(4-amino-2-(3,4,5-trimethoxyphenylamino)thieno[3,2-d]pyrimidin-7-yl)phenyl)acetamide;

N-(3-(4-amino-2-(3,4,5-trimethoxyphenylamino)thieno[3,2-d]pyrimidin-7-yl)phenyl)ethanesulfonamide;

1-(3-(4-amino-2-(3,4,5-trimethoxyphenylamino)thieno[3,2-d]pyrimidin-7-yl)phenyl)-3-butylurea;

N-(3-(4-amino-2-(3,4,5-trimethoxyphenylamino)thieno[3,2-d]pyrimidin-7-yl)phenyl)-2-(3,4-dimethoxyphenyl)acetamide;

N-(3-(4-amino-2-(3,4,5-trimethoxyphenylamino)thieno[3,2-d]pyrimidin-7-yl)phenyl)pyrazin-2-carboxamide;

N-(3-(4-amino-2-(3,4,5-trimethoxyphenylamino)thieno[3,2-d]pyrimidin-7-yl)phenyl)quinolin-6-carboxamide;

N-(3-(4-amino-2-(3,4,5-trimethoxyphenylamino)thieno[3,2-d]pyrimidin-7-yl)phenyl)-2,5-dimethylfuran-3-carboxamide;

N-(3-(4-amino-2-(3,4,5-trimethoxyphenylamino)thieno[3,2-d]pyrimidin-7-yl)phenyl)benzo[b]thiophen-2-carboxamide;

N-(3-(4-amino-2-(3,4,5-trimethoxyphenylamino)thieno[3,2-d]pyrimidin-7-yl)phenyl)-2-chloroisonicotinamide;

N-(3-(4-amino-2-(3,4,5-trimethoxyphenylamino)thieno[3,2-d]pyrimidin-7-yl)phenyl)thiazol-4-carboxamide;

3-(4-amino-2-(3,4,5-trimethoxyphenylamino)thieno[3,2-d]pyrimidin-7-yl)-N-methylbenzenesulfonamide;

N-(3-(4-amino-2-(6-(4-ethylpiperazin-1-yl)pyridin-3-ylamino)thieno[3,2-d]pyrimidin-7-yl)phenyl)methanesulfonamide;

N-(3-(4-amino-2-(6-morpholinopyrimidin-4-ylamino)thieno[3,2-d]pyrimidin-7-yl)phenyl)methanesulfonamide;

N-(3-(4-amino-2-(6-(4-ethylpiperazin-1-yl)pyrimidin-4-ylamino)thieno[3,2-d]pyrimidin-7-yl)phenyl)methanesulfonamide;

N-(3-(4-amino-2-(6-morpholinopyridin-3-ylamino)thieno[3,2-d]pyrimidin-7-yl)phenyl)methanesulfonamide;

N-(3-(4-amino-2-(4-(4-hydroxypiperidin-1-yl)phenylamino)thieno[3,2-d]pyrimidin-7-yl)phenyl)methanesulfonamide;
N-(3-(4-amino-2-(4-(4-ethylpiperazin-1-yl)phenylamino)thieno[3,2-d]pyrimidin-7-yl)phenyl)methanesulfonamide;
N-(3-(4-amino-2-(4-((4-ethylpiperazin-1-yl)methyl)phenylamino)thieno[3,2-d]pyrimidin-7-yl)phenyl)methanesulfonamide;
N-(3-(4-amino-2-(4-morpholinophenylamino)[3,2-d]pyrimidin-7-yl)phenyl)methanesulfonamide;
N-(3-(4-amino-2-(4-(2-(4-ethylpiperazin-1-yl)ethyl)phenylamino)thieno[3,2-d]pyrimidin-7-yl)phenyl)methanesulfonamide;
N-(3-(4-amino-2-(4-(4-(dimethylamino)piperidin-1-yl)phenylamino)thieno[3,2-d]pyrimidin-7-yl)phenyl)methanesulfonamide;
N-(3-(4-amino-2-(3-(4-ethylpiperazin-1-yl)phenylamino)thieno[3,2-d]pyrimidin-7-yl)phenyl)methanesulfonamide;
N-(3-(4-amino-2-(4-(4-(pyrrolidin-1-yl)piperidin-1-yl)phenylamino)thieno[3,2-d]pyrimidin-7-yl)phenyl)methanesulfonamide;
$N^2$-(6-(4-ethylpiperazin-1-yl)pyridin-3-yl)-7-(quinolin-3-yl)thieno[3,2-d]pyrimidin-2,4-diamine;
$N^2$-(4-morpholinophenyl)-7-(quinolin-3-yl)thieno[3,2-d]pyrimidin-2,4-diamine;
$N^2$-(4-(4-ethylpiperazin-1-yl)phenyl)-7-(quinolin-3-yl)thieno[3,2-d]pyrimidin-2,4-amine;
$N^2$-(6-morpholinopyridin-3-yl)-7-(quinolin-3-yl)thieno[3,2-d]pyrimidin-2,4-diamine;
$N^2$-(3-(4-ethylpiperazin-1-yl)phenyl)-7-(quinolin-3-yl)thieno[3,2-d]pyrimidin-2,4-diamine;
(S)-1-(4-(benzylamino)-7-ethynylthieno[3,2-d]pyrimidin-2-ylamino)propan-2-ol;
(S)-1-(7-ethynyl-4-((R)-1-phenylethylamino)thieno[3,2-d]pyrimidin-2-ylamino)propan-2-ol;
$N^4$-benzyl-$N^2$-(2-morpholinoethyl)-7-vinylthieno[3,2-d]pyrimidin-2,4-diamine;
(R)—$N^2$-(2-morpholinoethyl)-$N^4$-(1-phenylethyl)-7-vinylthieno[3,2-d]pyrimidin-2,4-diamine;
$N^4$-benzyl-7-ethyl-$N^2$-(2-morpholinoethyl)thieno[3,2-d]pyrimidin-2,4-diamine; and
3-(4-amino-2-(6-(4-ethylpiperazin-1-yl)pyridin-3-ylamino)thieno[3,2-d]pyrimidin-7-yl)-N-methylbenzamide hydrochloride.

The present invention also provides a method for preparing the 2,4,7-substituted thieno[3,2-d]pyrimidine compound represented by Chemical Formula 1. The preparation may be carried out according to Schemes 1 to 3 depending on the substituent ⒷーR$^b$ at the C-2 position.

According to Scheme 1, a 2,4,7-substituted thieno[3,2-d]pyrimidine compound represented by Chemical Formula 1 with ⒷーR$^b$ being phenyl or heteroaryl is prepared through two coupling reactions:

[Scheme 1]

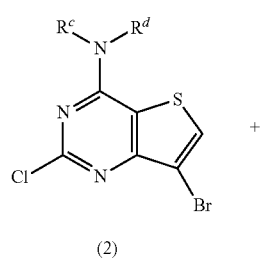

(2)

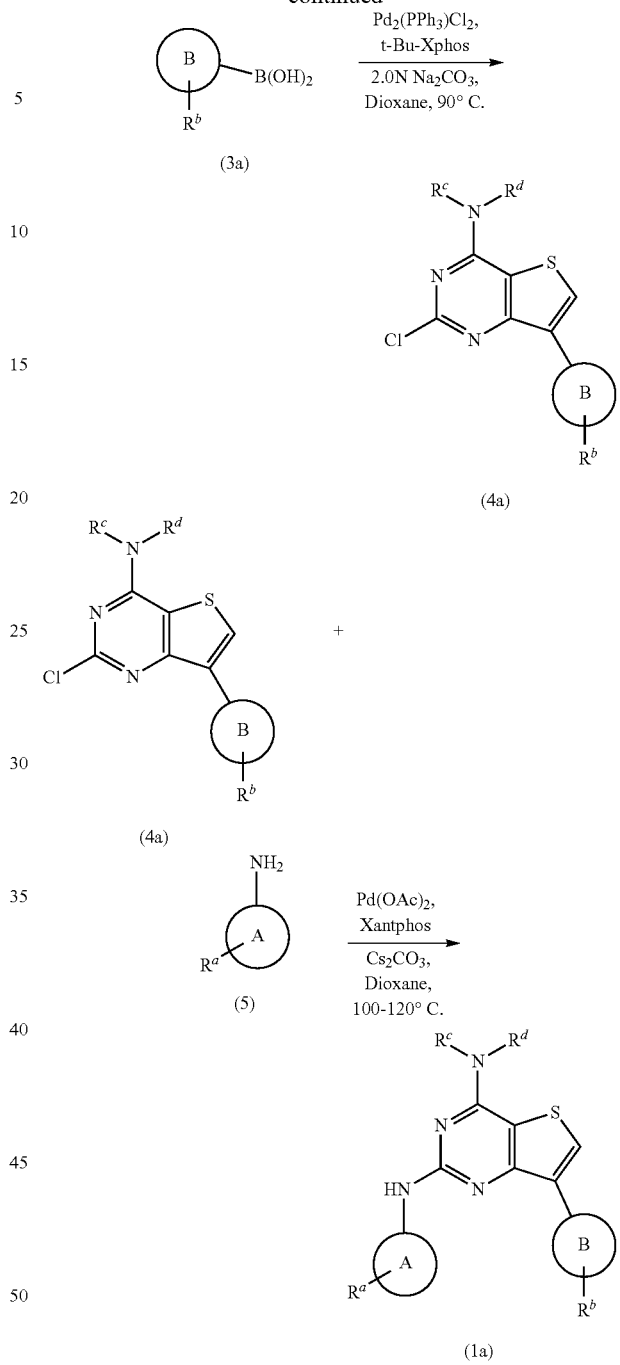

wherein A, R$^a$, R$^c$ and R$^d$ are the same as defined above and ⒷーR$^b$ represents phenyl or heteroaryl.

In the first coupling reaction, the 7-bromo-2-chloro-thieno[3,2-d]pyrimidin-4-amine compound represented by Chemical Formula 2 is subjected to Suzuki coupling reaction with the boronic acid compound represented by Chemical Formula 3a to prepare the compound represented by Chemical Formula 4a with B introduced at the C-7 position.

In the second coupling reaction, the compound represented by Chemical Formula 4a is subjected to Buchwald amination reaction with the amine compound represented by Chemical Formula 5 to prepare the target compound represented by Chemical Formula 1a.

In the Suzuki coupling reaction and the Buchwald amination reaction of Scheme 1, Pd$_2$(dba)$_3$, Pd(OAc)$_2$, PdCl$_2$(PPh$_3$)$_2$, Pd(PPh$_3$)$_4$, etc., may be used as a metal catalyst. And, Xantphos (CAS number: 161265-03-8), Davephos (CAS number: 213697-53-1), Johnphos (CAS number: 224311-51-7), X-phos (CAS number: 564483-18-7), tert-butyl Xphos (CAS number: 564483-19-8), etc., may be used as a ligand. And, carbonate, sulfate, phosphate, alkoxide, etc., of an alkali metal or alkaline earth metal may be used as a base. Specific examples include K$_2$CO$_3$, CsCO$_3$, Na$_2$CO$_3$, K$_3$PO$_4$, NaOt-Bu, KOt-Bu, or the like.

In the coupling reaction, a commonly used organic solvent including tetrahydrofuran, dioxane, N,N-dimethylformamide, N,N-dimethylsulfoxide, 2-butanol, 2-pentanol, or the like may be used as a reaction solvent. The reaction temperature is maintained at 50 to 200° C., preferably at 80 to 150° C.

According to Scheme 2, a 2,4,7-substituted thieno[3,2-d]pyrimidine compound represented by Chemical Formula 1 with Ⓑ—R$^b$ being vinyl is prepared as follows:

[Scheme 2]

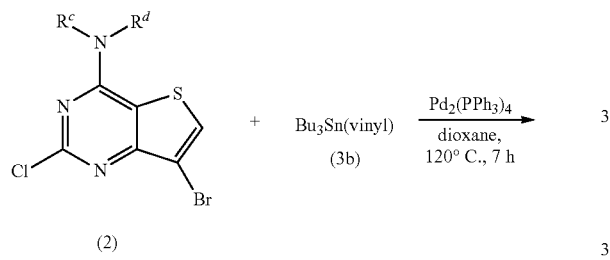

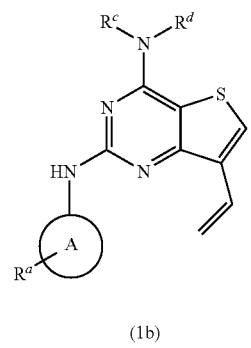

(1b)

wherein A, R$^a$, R$^c$ and R$^d$ are the same as defined above.

First, the 7-bromo-2-chloro-thieno[3,2-d]pyrimidin-4-amine compound represented by Chemical Formula 2 is subjected to Stille coupling reaction with tributyl(vinyl)tin to prepare the compound represented by Chemical Formula 4b with vinyl introduced at the C-7 position. The Stille coupling reaction is carried out at a temperature range of 80 to 150° C. using Pd$_2$(dba)$_3$, Pd(OAc)$_2$, PdCl$_2$(PPh$_3$)$_2$, Pd(PPh$_3$)$_4$, or the like as a metal catalyst.

Then, the compound represented by Chemical Formula 4b is subjected to a coupling reaction with the amine compound represented by Chemical Formula 5 to prepare the target compound represented by Chemical Formula 1b. The coupling reaction is carried out at a temperature range of 80° to 150° C.

According to Scheme 3, a 2,4,7-substituted thieno[3,2-d]pyrimidine compound represented by Chemical Formula 1 with Ⓑ—R$^b$ being ethynyl is prepared as follows:

[Scheme 3]

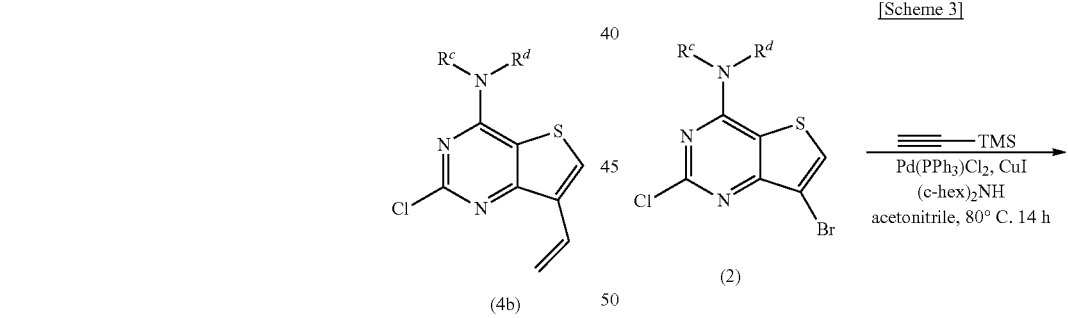

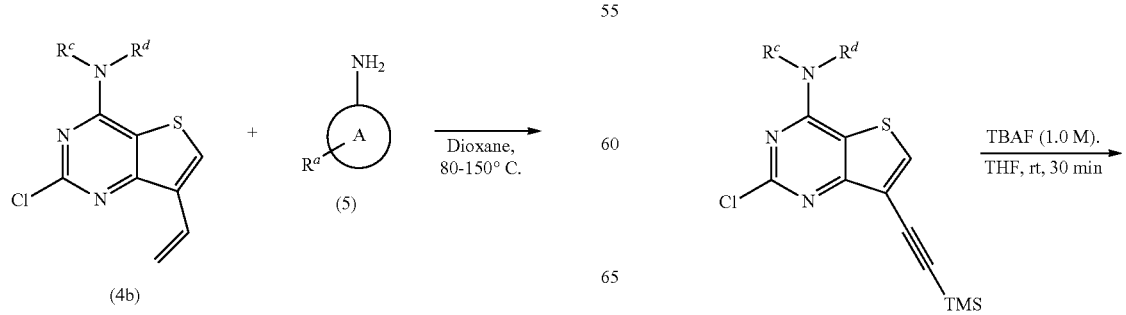

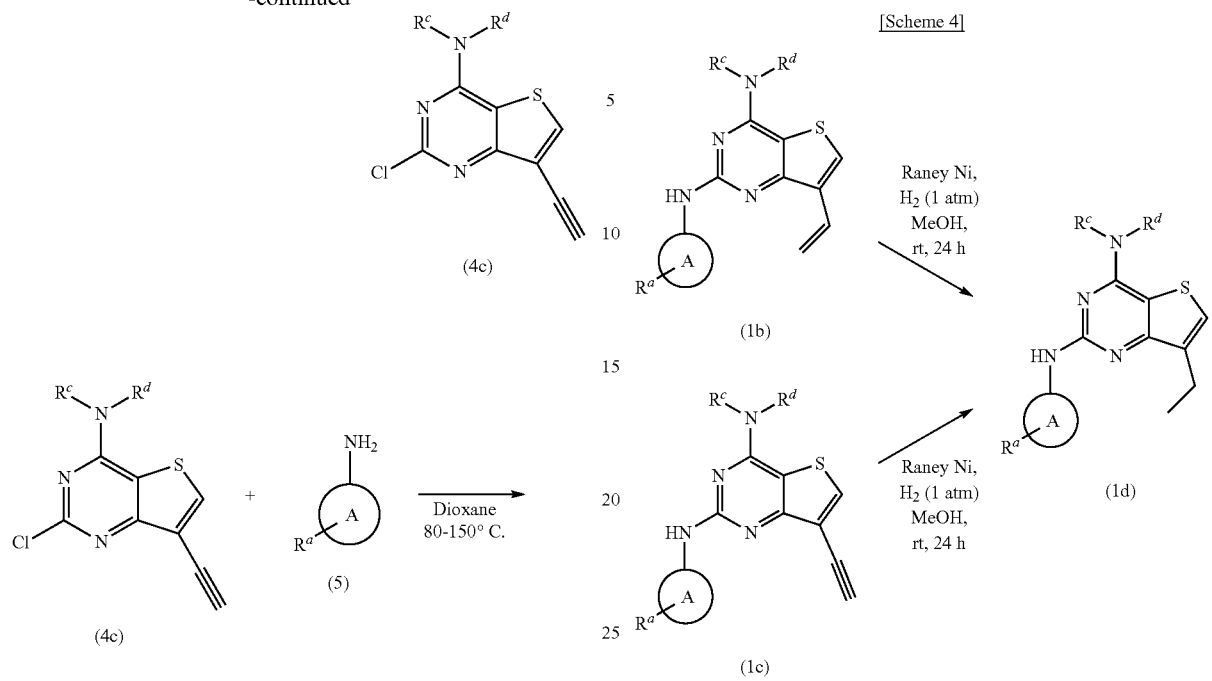

wherein A, $R^a$, $R^c$ and $R^d$ are the same as defined above.

First, the 7-bromo-2-chloro-thieno[3,2-d]pyrimidin-4-amine compound represented by Chemical Formula 2 is subjected to Sonogashira reaction with ethynyltrimethylsilane to introduce trimethylsilylethynyl at the C-7 position, and then reacted by stirring at room temperature after adding tetrabutylammonium fluoride (TBAF) to remove the trimethylsilyl (TMS) group, so as to prepare the compound represented by Chemical Formula 4c with ethynyl introduced at the C-7 position. The Sonogashira reaction may be performed in the presence of copper iodide and dialkylamine, using $Pd_2(dba)_3$, $Pd(OAc)_2$, $PdCl_2(PPh_3)_2$, $Pd(PPh_3)_4$, or the like as a metal catalyst.

Then, the compound represented by Chemical Formula 4c is subjected to a coupling reaction with the amine compound represented by Chemical Formula 5 to prepare the target compound represented by Chemical Formula 1c.

According to Scheme 4, a 2,4,7-substituted thieno[3,2-d]pyrimidine compound represented by Chemical Formula 1 with ⒷーR^b being ethyl is prepared by reducing the compound represented by Chemical Formula 1b or 1c with ⒷーR^b being vinyl or ethynyl:

wherein A, $R^a$, $R^c$ and $R^d$ are the same as defined above.

The reduction may be performed by reducing the double or triple bond using Raney nickel (Ni), Pd/C or $Pd(OH)_2$.

The 7-bromo-2-chlorothieno[3,2-d]pyrimidin-4-amine compound represented by Chemical Formula 2, which is used as a starting material in Schemes 1, 2 and 3 may be prepared according to Scheme 5:

[Scheme 5]

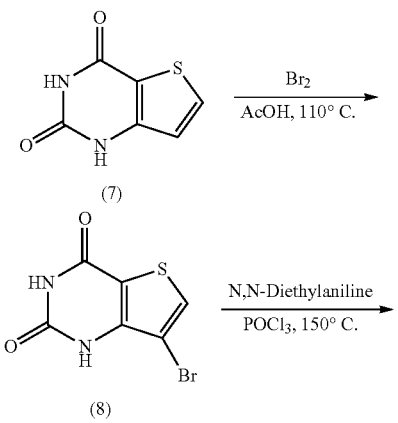

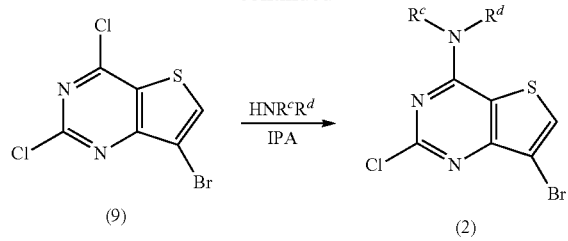

wherein $R^c$ and $R^d$ are the same as defined above.

According to Scheme 5, the 7-bromo-2-chlorothieno[3,2-d]pyrimidin-4-amine compound represented by Chemical Formula 2 is prepared through the following 4-step process.

In the first step, a pyrimidin-2,4-dione backbone is formed through cyclization of the amino group and the ester group of the methyl 3-aminothiophen-2-carboxylate compound represented by Chemical Formula 6, using sodium cyanate (NaOCN).

In the second step, a bromo group is introduced at the C-7 position of the thieno[3,2-d]pyrimidin-2,4(1H,3H)-dione compound represented by Chemical Formula 7. This step may be performed at high temperature (110° C.) using bromine in the presence of acetic acid.

In the third step, the pyrimidin-2,4(1H,3H)-dione ring of the compound represented by Chemical Formula 8 is converted into a 2,4-dichloropyrimidine ring. This step may be performed at high temperature (150° C.) using phosphorus oxychloride ($POCl_3$) in the presence of N,N-dimethylaniline.

Finally, in the fourth step, the chloro group at the C-4 position of the 7-bromo-2,4-dichlorothieno[3,2-d]pyrimidine represented by Chemical Formula 9 is substituted by an amino group. This step may be performed using various corresponding amine compounds in an isopropyl alcohol (IPA) solvent.

The 2,4,7-substituted thieno[3,2-d]pyrimidine compound represented by Chemical Formula 1, an isomer thereof, a pharmaceutically acceptable salt thereof, a solvate thereof and a hydrate thereof may be used as an agent for preventing or treating cancers caused by abnormal cell growth because they exhibit superior inhibition activity against various protein kinases, e.g., ALK, Abl, CDK, Aurora, EphA1, FAK, Flt3, Fms, Itk, KDR, Kit, Met, Ret, Raf, Src, Syk, Tie2 and TrkB. Examples of the diseases caused by abnormal cell growth include various cancers such as stomach cancer, lung cancer, liver cancer, colorectal cancer, small intestine cancer, pancreatic cancer, brain cancer, bone cancer, melanoma, breast cancer, sclerosing adenoma, uterine cancer, cervical cancer, head and neck cancer, esophageal cancer, thyroid cancer, parathyroid cancer, renal cancer, sarcoma, prostate cancer, urethral cancer, bladder cancer, leukemia, multiple myeloma, hematological malignancy such as myelodysplastic syndrome, lymphoma such as Hodgkin's disease and non-Hodgkin lymphoma, fibroadenoma, or the like.

Accordingly, the present invention provides a pharmaceutical composition comprising the 2,4,7-substituted thieno[3,2-d]pyrimidine compound represented by Chemical Formula 1, a pharmaceutically acceptable salt thereof, a solvate thereof or a hydrate thereof as an effective ingredient, and an agent for preventing and treating various cancers caused by abnormal cell growth.

The pharmaceutical composition of the present invention comprises the 2,4,7-substituted thieno[3,2-d]pyrimidine compound represented by Chemical Formula 1, a pharmaceutically acceptable salt thereof, a solvate thereof or a hydrate thereof as an effective ingredient and may further include a commonly used, nontoxic, pharmaceutically acceptable carrier, adjuvant, excipient, etc., to prepare formulations commonly used in the pharmaceutical field, for example, formulations for oral administration such as tablet, capsule, troche, liquid, suspension, etc., and formulations for parenteral administration.

The excipient that may be used in the pharmaceutical composition of the present invention includes sweetener, binder, solubilizer, wetting agent, emulsifier, isotonic agent, adsorbent, disintegrant, antioxidant, preservative, lubricant, filler, aromatic, or the like. For example, lactose, dextrose, sucrose, mannitol, sorbitol, cellulose, glycine, silica, talc, stearic acid, stearin, magnesium stearate, magnesium aluminum silicate, starch, gelatin, gum tragacanth, alginic acid, sodium alginate, methylcellulose, sodium carboxymethylcellulose, agar, water, ethanol, polyethylene glycol, polyvinylpyrrolidone, sodium chloride, calcium chloride, orange essence, strawberry essence, vanilla flavor, etc., may be used.

The administration dose of the compound according to the present invention may vary depending on the patient's age, body weight, sex and physical conditions, administration type, severity of disease, etc. Based on an adult patient weighing 70 kg, the administration dose may be in general 0.01 to 1,000 mg/day. As per the decision by a physician or a pharmacist, the administration may be once to several times a day with predetermined time intervals.

MODE FOR INVENTION

The examples, formulation examples and test examples will now be described.

The following examples, formulation examples and test examples are for illustrative purposes only and not intended to limit the scope of the present invention.

EXAMPLES

Example 1

3-(4-amino-2-(6-(4-ethylpiperazin-1-yl)pyridin-3-ylamino)thieno[3,2-d]pyrimidin-7-yl)-N-methylbenzamide

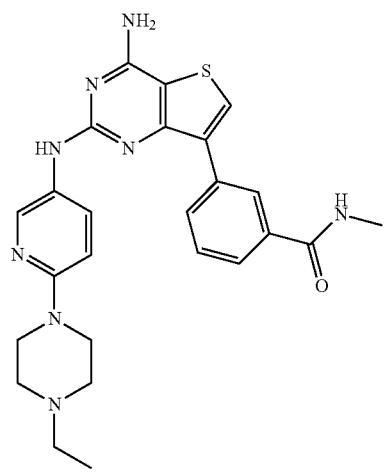 [SMILES: CCN1CCN(c2ccc(Nc3nc(N)c4scc(-c5cccc(C(=O)NC)c5)c4n3)cn2)CC1]

The compound represented by the above structural formula was prepared through a 9-step synthesis process as follows.

Step 1: thieno[3,2-d]pyridin-2,4(1H,3H)-dione

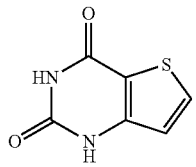 [SMILES: O=c1[nH]c(=O)c2sccc2[nH]1]

To a solution in which sodium cyanate (5.0 g, 77.0 mmol) was dissolved in water (15.0 mL), methyl 3-aminothiophen-2-carboxylate (6.05 g, 38.4 mmol) dissolved in a mixture solution (90 mL) of 50% glacial acetic acid and water was slowly added dropwise. After stirring for 5 hours at room temperature, thus prepared white precipitate was filtered. The white solid was dissolved in 2.0 N sodium hydroxide solution (90.0 mL). The mixture solution was cooled to 0° C. and acidified using acetic acid. Filtration of thus prepared white solid followed by drying yielded the target compound (5.2 g, 81% yield).

$^1$H NMR (400 MHz, DMSO-$d_6$) δ 11.33 (bs, 2H), 8.10 (d, J=5.2 Hz, 1H), 8.10 (d, J=5.2 Hz, 1H), MS m/z: 168.94 [M+1].

Step 2: 7-bromothieno[3,2-d]pyrimidin-2,4(1H,3H)-dione

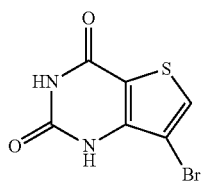 [SMILES: O=c1[nH]c(=O)c2scc(Br)c2[nH]1]

To a solution in which thieno[3,2-d]pyrimidin-2,4(1H,3H)-dione (5.0 g, 29.5 mmol) was dissolved in glacial acetic acid (200 mL), bromine (4.55 mL, 89.0 mmol) was added. The reaction mixture solution was stirred at 110° C. for 30 hours, cooled to room temperature, and then slowly added to ice water (400 mL). Drying of thus prepared solid followed by filtration, washing several times with water and drying yielded the target compound (6.5 g, 90% yield).

$^1$H NMR (400 MHz, DMSO-$d_6$) δ 11.54 (s, 1H), 11.42 (s, 1H), 8.24 (s, 1H), MS m/z: 247.34, 249.32 [M+1].

Step 3: 7-bromo-2,4-dichlorothieno[3,2-d]pyrimidine

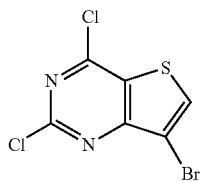 [SMILES: Clc1nc(Cl)c2scc(Br)c2n1]

Phosphoryl chloride (24.6 mL, 267 mmol) was added 7-bromothieno[3,2-d]pyrimidin-2,4(1H,3H)-dione (6.6 g, 26.7 mmol), and then N,N-diethylaniline (17.1 mL, 106.8 mmol) was slowly added thereto. The reaction mixture solution was stirred at 150° C. for 5 hours. The mixture solution was cooled to room temperature and then slowly added to ice water (300 mL). Washing of thus prepared solid with ice water followed by drying yielded the target compound (6.2 g, 82% yield).

$^1$H NMR (400 MHz, DMSO-$d_6$) δ 8.40 (s, 1H), MS m/z: 282.96, 284.96, 286.96 [M+1].

Step 4: 7-bromo-2-chlorothieno[3,2-d]pyrimidin-4-amine

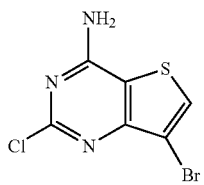 [SMILES: Nc1nc(Cl)nc2c(Br)csc12]

7-Bromo-2,4-dichlorothieno[3,2-d]pyrimidine (3.0 g, 10.64 mmol) was added to a sealed reactor and 2.0 N ammonia isopropanol (26.6 mL, 53.2 mmol) was added thereto. The reaction mixture was stirred at 80° C. for 5 hours and then cooled to room temperature. The reaction mixture was added to ice water (100 mL). Thus prepared solid was filtered and dried by blowing nitrogen gas. The resultant target compound (2.1 g, 75% yield) was used in the following reaction without purification.

$^1$H NMR (400 MHz, DMSO-$d_6$) δ 8.36 (s, 1H), 8.19 (s, 2H), MS m/z: 263.95, 265.94, 267.95 [M+1].

Step 5: 3-(4-amino-2-chlorothieno[3,2-d]pyrimidin-7-yl)benzoic acid

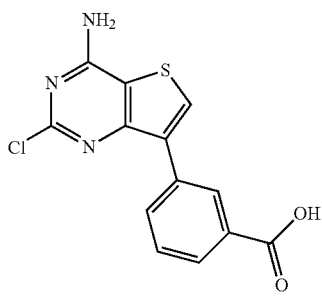 [SMILES: Nc1nc(Cl)nc2c(-c3cccc(C(=O)O)c3)csc12]

7-Bromo-2-chlorothieno[3,2-d]pyrimidin-4-amine (500 mg, 1.90 mmol) was dissolved in dioxane (10 mL) and 2.0 N sodium carbonate (2.85 mL, 5.70 mmol) and 3-boronobenzoic acid (316 mg, 1.90 mmol) were added. Nitrogen was flown to the mixture solution for 10 minutes and then Pd$_2$(PPh$_3$)Cl$_2$ (80 mg, 0.11 mmol) and t-ButylXphos (73 mg, 0.17 mmol) were added. The reaction mixture solution was stirred at 90° C. for 6 hours and then filtered with celite. The organic layer was concentrated and then 2.0 N sodium hydroxide solution was added until the pH reached 10. After extracting with ethyl acetate, the aqueous layer was adjusted to pH 5 by adding 2.0 N hydrochloric acid solution. Thus prepared white solid was filtered and dried using nitrogen gas. The resultant target compound (380 mg, 65% yield) was used in the following reaction without purification.

Step 6: 3-(4-amino-2-chlorothieno[3,2-d]pyrimidin-7-yl)-N-methylbenzamide

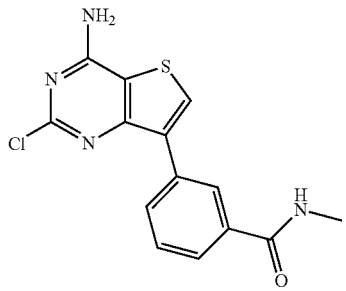 [SMILES: CNC(=O)c1cccc(-c2csc3c(N)nc(Cl)nc23)c1]

3-(4-Amino-2-chlorothieno[3,2-d]pyrimidin-7-yl)benzoic acid (300 mg, 0.98 mmol) was dissolved in N,N-dimethylformamide (5 mL) and then methylamine hydrochloride (329 mg, 4.91 mmol), 1-ethyl-3-(3-dimethylaminopropyl)carbodiimide (282 mg, 1.47 mmol), hydroxybenzotriazole (239 mg, 1.76 mmol) and trimethylamine (0.889 mL, 6.38 mmol) were added. The reaction mixture was stirred at room temperature for a day. The reaction mixture was diluted with ethyl acetate and then washed with ammonium chloride aqueous solution. The organic layer was dried with magnesium sulfate, filtered with celite and then concentrated. Purification by chromatography (1/4 ethyl acetate/hexane) yielded the target compound (280 mg, 89% yield).

Step 7: 1-ethyl-4-(5-nitropyridin-2-yl)piperazine

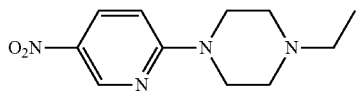 [SMILES: CCN1CCN(c2ccc([N+](=O)[O-])cn2)CC1]

2-Chloro-5-nitropyridine (800 mg, 5.05 mmol) was dissolved in dioxane (20 mL) and then 1-ethylpiperazine (1.7 g, 15.15 mmol) and N,N-diisopropylethylamine (927 mL, 5.05 mmol) were added. The reaction mixture solution was stirred at 70° C. for a day. The reaction solution was cooled to room temperature, diluted with ethyl acetate, and then washed with brine. The organic layer was concentrated by drying with magnesium sulfate. The target compound (1.05 g, 87% yield) was used in the following reaction without purification.
MS m/z: 237.51 [M+1].

Step 8: 6-(4-ethylpiperazin-1-yl)pyridin-3-amine

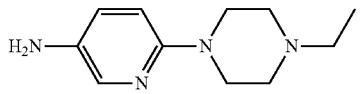

1-Ethyl-4-(5-nitropyridin-2-yl)piperazine (3.09 g, 13.8 mmol) was dissolved in methanol (69 mL) and 10% Pd/C (300 mg) was added. The reaction mixture was stirred at room temperature for a day under a pressure of a balloon filled with hydrogen gas. The reaction mixture solution was concentrated by filtering with celite. The resultant target compound (2.4 g, 89% yield) was used in the following reaction without purification.
$^1$H NMR (400 MHz, DMSO-$d_6$) δ 7.59 (d, J=2.8 Hz, 1H), 6.89 (dd, J=2.8 Hz, J=8.8 Hz, 1H), 6.63 (d, J=7.2 Hz, 1H), 4.54 (s, 2H), 3.18 (m, 4H), 2.42 (m, 4H), 2.32 (q, 2H), 1.01 (t, 3H), MS m/z: 207.44 [M+1].

Step 9

3-(4-amino-2-(6-(4-ethylpiperazin-1-yl)pyridin-3-ylamino)thieno[3,2-d]pyrimidin-7-yl)-N-methylbenzamide 3-(4-Amino-2-chlorothieno[3,2-d]pyrimidin-7-yl)-N-methylbenzamide (20 mg, 0.063 mmol) was dissolved in dioxane (1 mL) and then sodium hydroxide (13 mg, 0.31 mmol) and 6-(4-ethylpiperazin-1-yl)pyridin-3-amine (19 mg, 0.094 mmol) were added. After flowing nitrogen gas to the reaction mixture for 10 minutes, Pd$_2$(dba)$_3$ (4 mg, 0.004 mmol) and X-phos (1 mg, 0.12 mmol) were added. The reaction mixture was stirred at 120° C. for 2 hours and filtered with celite. The filtrate was diluted with ethyl acetate and then washed with brine. The organic layer was dried with magnesium sulfate, filtered with celite, and then concentrated. Purification by chromatography (5% methanol/dichloromethane) yielded the target compound (17 mg, 55% yield) of Example 1.
MS m/z: 489.08 [M+1].

Examples 2 to 10

The target compounds of Examples 2 to 10 were prepared through Buchwald amination reaction of the 3-(4-amino-2-chlorothieno[3,2-d]pyrimidin-7-yl)-N-methylbenzamide synthesized in Step 6 of Example 1 with various amine compounds, according to the following reaction scheme. The condition of the Buchwald amination reaction was the same as in Step 9 of Example 1.

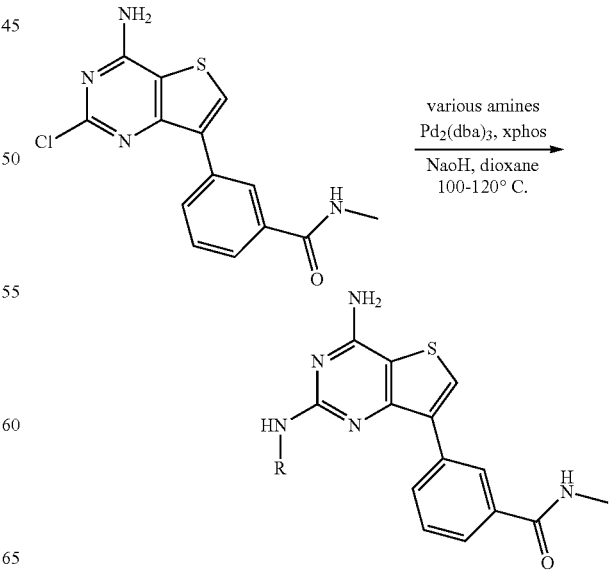

Example 2

3-(4-amino-2-(6-morpholinopyridin-3-ylamino)thieno[3,2-d]pyrimidin-7-yl)-N-methylbenzamide

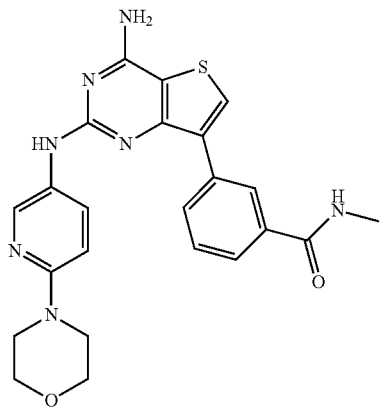 [SMILES: CNC(=O)c1cccc(-c2csc3c(N)nc(Nc4ccc(N5CCOCC5)nc4)nc23)c1]

MS m/z: 462.04 [M+1].

Example 3

3-(4-amino-2-(4-(4-hydroxypiperidin-1-yl)phenylamino)thieno[3,2-d]pyrimidin-7-yl)-N-methylbenzamide

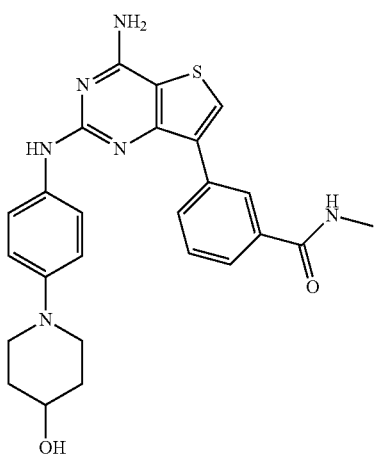 [SMILES: CNC(=O)c1cccc(-c2csc3c(N)nc(Nc4ccc(N5CCC(O)CC5)cc4)nc23)c1]

MS m/z: 475.04 [M+1].

Example 4

3-(4-amino-2-(4-(1-ethylpiperidin-4-yl)phenylamino)thieno[3,2-d]pyrimidin-7-yl)-N-methylbenzamide

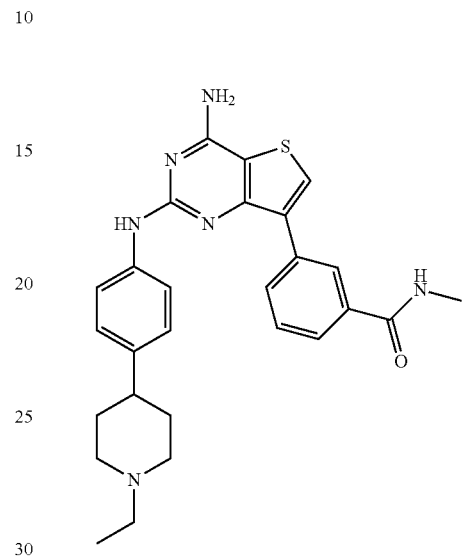

MS m/z: 487.07 [M+1].

Example 5

3-(4-amino-2-(3-(4-ethylpiperazin-1-yl)phenylamino)thieno[3,2-d]pyrimidin-7-yl)-N-methylbenzamide

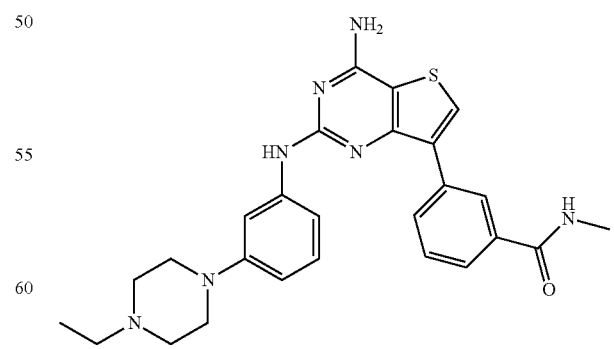

MS m/z: 488.07 [M+1].

Example 6

3-(4-amino-2-(4-(4-ethylpiperazin-1-yl)phenylamino)thieno[3,2-d]pyrimidin-7-yl)-N-methylbenzamide

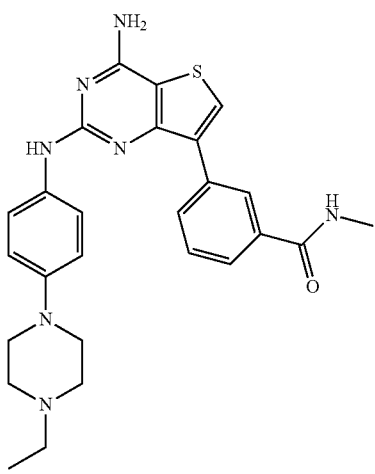 [SMILES: CCN1CCN(c2ccc(Nc3nc(N)c4scc(-c5cccc(C(=O)NC)c5)c4n3)cc2)CC1]

MS m/z: 488.07 [M+1].

Example 7

3-(4-amino-2-(4-(4-(pyrrolidin-1-yl)piperidin-1-yl)phenylamino)thieno[3,2-d]pyrimidin-7-yl)-N-methylbenzamide

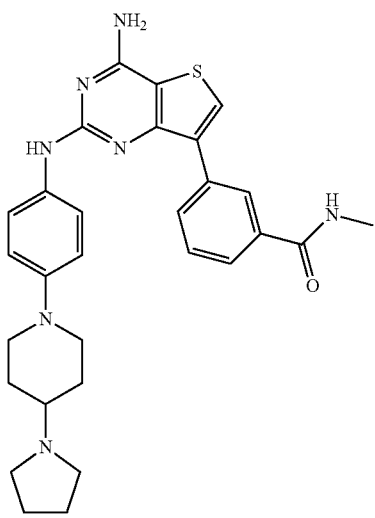 [SMILES: CNC(=O)c1cccc(-c2csc3c(N)nc(Nc4ccc(N5CCC(N6CCCC6)CC5)cc4)nc23)c1]

MS m/z: 528.10 [M+1].

Example 8

3-(4-amino-2-(6-morpholinopyrimidin-4-ylamino)thieno[3,2-d]pyrimidin-7-yl)-N-methylbenzamide

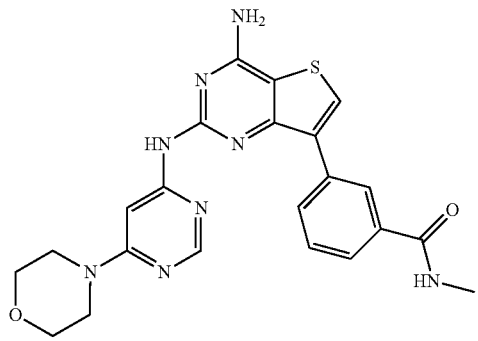 [SMILES: CNC(=O)c1cccc(-c2csc3c(N)nc(Nc4cc(N5CCOCC5)ncn4)nc23)c1]

MS m/z: 462.97 [M+1].

Example 9

3-(4-amino-2-(6-(4-ethylpiperazin-1-yl)pyrimidin-4-ylamino)thieno[3,2-d]pyrimidin-7-yl)-N-methylbenzamide

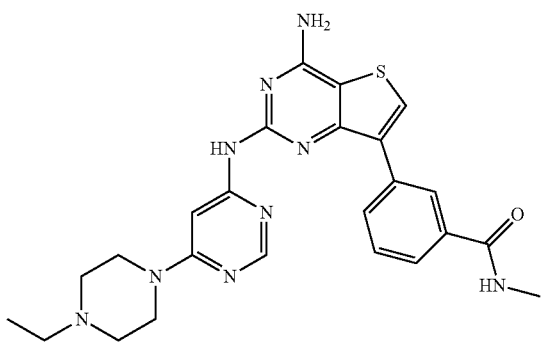 [SMILES: CCN1CCN(c2cc(Nc3nc(N)c4scc(-c5cccc(C(=O)NC)c5)c4n3)ncn2)CC1]

MS m/z: 490.04 [M+1].

Example 10

3-(4-amino-2-(2-methoxy-4-morpholinophenylamino)thieno[3,2-d]pyrimidin-7-yl)-N-methylbenzamide

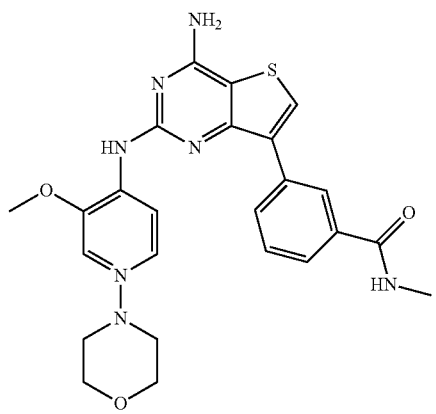

MS m/z: 491.02 [M+1].

Example 11

7-(3-aminophenyl)-N²-(3,4,5-trimethoxyphenyl)thieno[3,2-d]pyrimidin-2,4-diamine

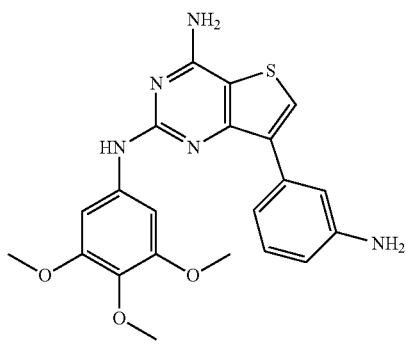 [SMILES: COc1cc(Nc2nc(N)c3scc(-c4cccc(N)c4)c3n2)cc(OC)c1OC]

The compound of Example 11 was prepared through a 3-step synthesis process as follows.

Step 1. 2-chloro-7-(3-nitrophenyl)thieno[3,2-d]pyrimidin-4-amine

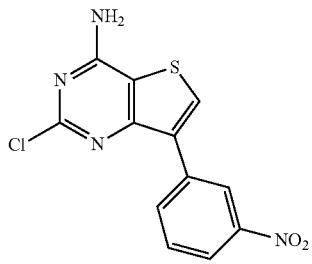 [SMILES: Nc1nc(Cl)nc2c(-c3cccc([N+](=O)[O-])c3)csc12]

7-Bromo-2-chlorothieno[3,2-d]pyrimidin-4-amine (500 mg, 1.90 mmol) was dissolved in dioxane (10 mL) and then 2.0 N sodium carbonate (2.85 mL, 5.70 mmol) and 3-nitrophenylboronic acid (320 mg, 1.90 mmol) were added. After flowing nitrogen to the mixture solution for 10 minutes, Pd₂(PPh₃)Cl₂ (80 mg, 0.11 mmol) and t-Butyl Xphos (73 mg, 0.17 mmol) were added. The reaction mixture solution was stirred at 90° C. for 6 hours, filtered with celite, and washed with ethyl acetate. The aqueous layer was separated from the organic layer and extracted with ethyl acetate. The organic layer was combined, washed with brine, dried with MgSO₄, and then concentrated by filtering. Purification by silica gel chromatography (1/4 to 1/3 ethyl acetate/hexane) yielded the target compound (420 mg, 72% yield).

MS m/z: 462.04 [M+1].

Step 2

7-(3-ni phenyl)-N²-(3,4,5-trimethoxyphenyl)thieno[3,2-d]pyrimidin-2,4-diamine

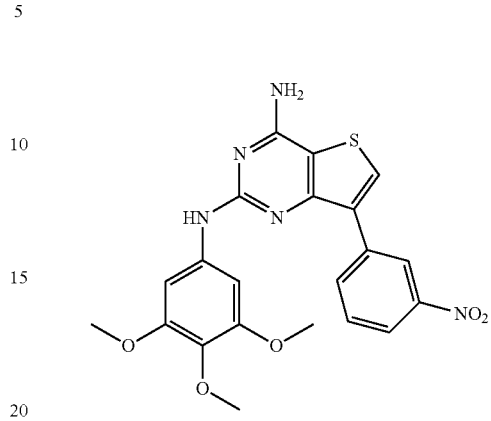

The target compound (445 mg, 75% yield) was obtained in the same manner as Step 9 of Example 1, using 2-chloro-7-(3-nitrophenyl)thieno[3,2-d]pyrimidin-4-amine (400 mg, 1.30 mmol) and 3,4,5-trimethoxybenzenamine (479 mg, 2.61 mmol).

Step 3

7-(3-aminophenyl)-N²-(3,4,5-trimethoxyphenyl)thieno[3,2-d]pyrimidin-2,4-diamine 7-(3-Nitrophenyl)-N²-(3,4,5-trimethoxyphenyl)thieno[3,2-d]pyrimidin-2,4-diamine (400 mg, 0.88 mmol) was dissolved in ethanol (3.0 mL) and tin(II) chloride dihydrate (996 mg, 4.41 mmol) was added. The reaction mixture was stirred at 80° C. for 2 hours. After removing ethanol by distillation under reduced pressure, ammonia water was slowly added to make pH 5. Sodium carbonate was added to thus prepared yellow precipitate until the pH reached 7. The precipitate was filtered and washed several times with ethyl acetate. Concentration of the filtrate yielded the target compound of Example 11 (320 mg, 85% yield).

MS m/z: 424.43 [M+1].

Example 12

1-(3-(4-amino-2-(3,4,5-trimethoxyphenylamino)thieno[3,2-d]pyrimidin-7-yl)phenyl)-3-isopropylurea

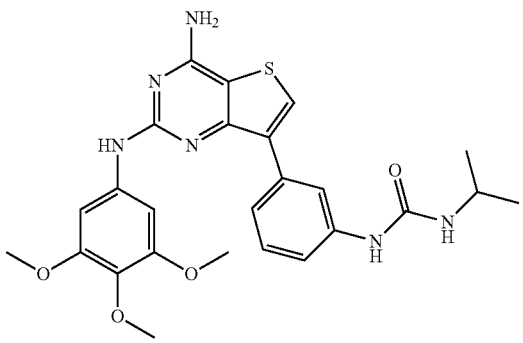 [SMILES: COc1cc(Nc2nc(N)c3scc(-c4cccc(NC(=O)NC(C)C)c4)c3n2)cc(OC)c1OC]

The 7-(3-aminophenyl)-N²-(3,4,5-trimethoxyphenyl)thieno[3,2-d]pyrimidin-2,4-diamine (20 mg, 0.047 mmol) synthesized in Example 11 was dissolved in anhydrous tetrahydrofuran (1 mL) and then triethylamine (20 μL, 0.14 mmol) and isopropyl isocyanate (5 mg, 0.057 mmol) were added. After stirring at room temperature for 4 hours, ethyl acetate (2 mL) was added and the mixture was washed with brine. After drying with MgSO₄, the product was filtered and concentrated. Purification by silica gel chromatography (ethyl acetate/hexane, 1/1) yielded the target compound of Example 12 (18 mg, 75% yield).

¹H NMR (400 MHz, DMSO-d₆) δ 9.77 (s, 1H), 9.14 (s, 1H), 8.60 (d, 1H), 8.43 (s, 1H), 8.22 (s, 1H), 8.14 (s, 1H), 7.65 (s, 1H), 7.49 (m, 1H), 7.21 (s, 2H), 6.95 (s, 2H), 3.94 (m, 1H), 3.60 (s, 6H), 3.52 (s, 3H), 1.17 (d, 6H), MS m/z: 509.58 [M+1].

Examples 13 to 25

The target compounds of Examples 13 to 25 were prepared through reaction with amide, sulfonamide or urea using the 7-(3-aminophenyl)-N²-(3,4,5-trimethoxyphenyl)thieno[3,2-d]pyrimidin-2,4-diamine synthesized in Example 11 and various acyl chloride, sulfonyl chloride, benzoic acid and isocyanate.

Example 13

N-(3-(4-amino-2-(3,4,5-trimethoxyphenylamino)thieno[3,2-d]pyrimidin-7-yl)phenyl)methanesulfonamide

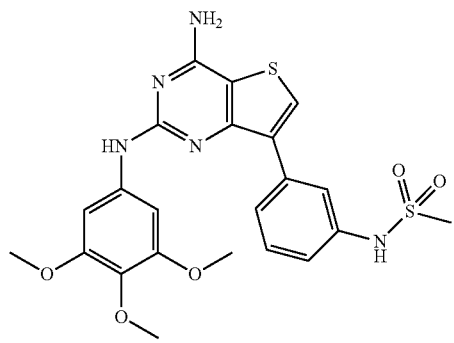

MS m/z: 502.45 [M+1].

Example 14

1-(3-(4-amino-2-(3,4,5-trimethoxyphenylamino)thieno[3,2-d]pyrimidin-7-yl)phenyl)-3-(4-chloro-3-(trifluoromethyl)phenyl)urea

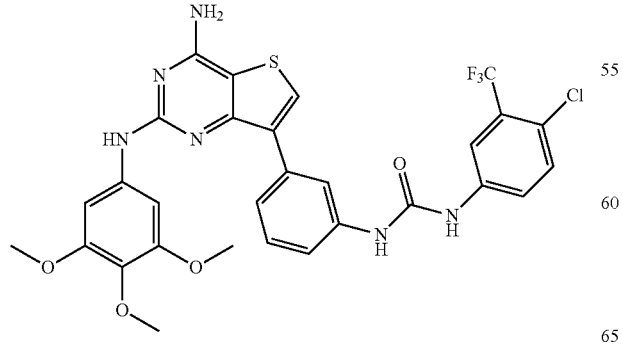

MS m/z: 630.39 [M+1].

Example 15

N-(3-(4-amino-2-(3,4,5-trimethoxyphenylamino)thieno[3,2-d]pyrimidin-7-yl)phenyl)cyclopropanecarboxamide

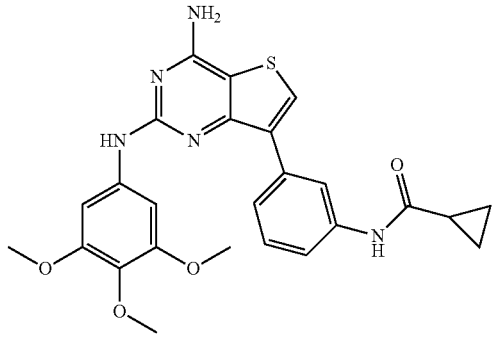 [SMILES: COc1cc(Nc2nc(N)c3scc(-c4cccc(NC(=O)C5CC5)c4)c3n2)cc(OC)c1OC]

MS m/z: 492.39 [M+1].

Example 16

N-(3-(4-amino-2-(3,4,5-trimethoxyphenylamino)thieno[3,2-d]pyrimidin-7-yl)phenyl)acetamide

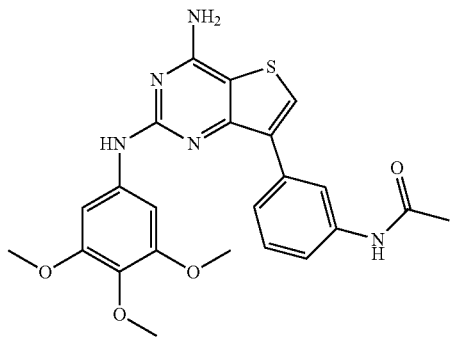 [SMILES: COc1cc(Nc2nc(N)c3scc(-c4cccc(NC(C)=O)c4)c3n2)cc(OC)c1OC]

MS m/z: 466.38 [M+1].

Example 17

N-(3-(4-amino-2-(3,4,5-trimethoxyphenylamino)thieno[3,2-d]pyrimidin-7-yl)phenyl)ethanesulfonamide

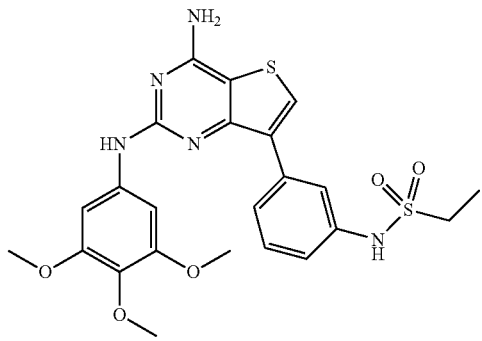 [SMILES: CCS(=O)(=O)Nc1cccc(-c2csc3c(N)nc(Nc4cc(OC)c(OC)c(OC)c4)nc23)c1]

MS m/z: 516.50 [M+1].

Example 18

1-(3-(4-amino-2-(3,4,5-trimethoxyphenylamino)thieno[3,2-d]pyrimidin-7-yl)phenyl)-3-butylurea

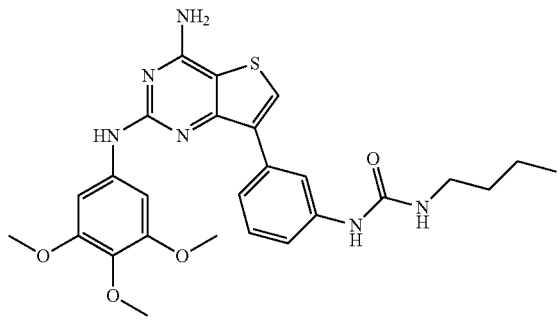 [SMILES: CCCCNC(=O)Nc1cccc(-c2csc3c(N)nc(Nc4cc(OC)c(OC)c(OC)c4)nc23)c1]

MS m/z: 522.89 [M+1].

Example 19

N-(3-(4-amino-2-(3,4,5-trimethoxyphenylamino)thieno[3,2-d]pyrimidin-7-yl)phenyl)-2-(3,4-dimethoxyphenyl)acetamide

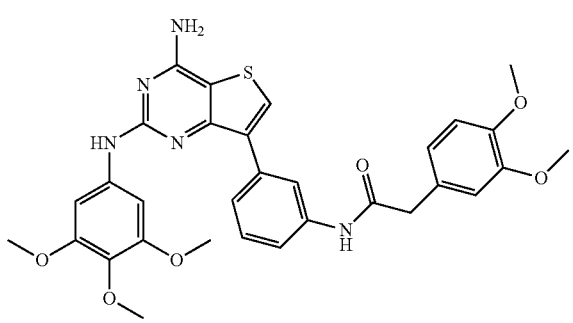

MS m/z: 601.96 [M+1].

Example 20

N-(3-(4-amino-2-(3,4,5-trimethoxyphenylamino)thieno[3,2-d]pyrimidin-7-yl)phenyl)pyrazin-2-carboxamide

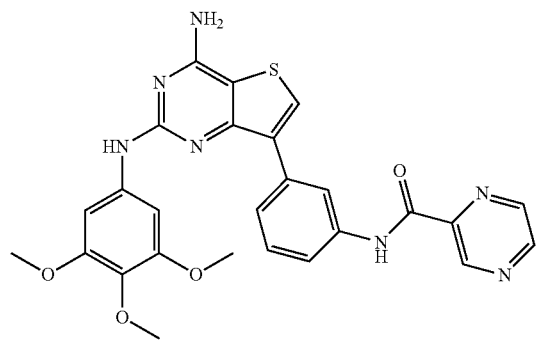 [SMILES: COc1cc(Nc2nc(N)c3scc(-c4cccc(NC(=O)c5cnccn5)c4)c3n2)cc(OC)c1OC]

MS m/z: 529.94 [M+1].

Example 21

N-(3-(4-amino-2-(3,4,5-trimethoxyphenylamino)thieno[3,2-d]pyrimidin-7-yl)phenyl)quinolin-6-carboxamide

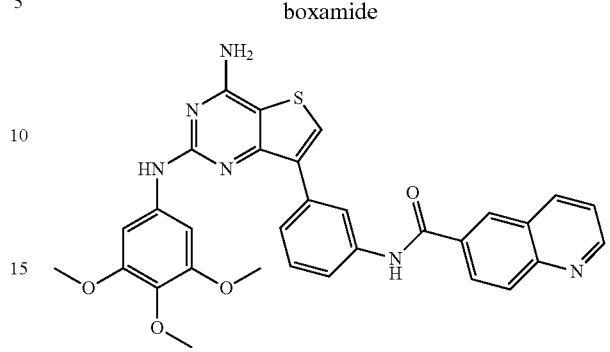

MS m/z: 578.96 [M+1].

Example 22

N-(3-(4-amino-2-(3,4,5-trimethoxyphenylamino)thieno[3,2-d]pyrimidin-7-yl)phenyl)-2,5-dimethylfuran-3-carboxamide

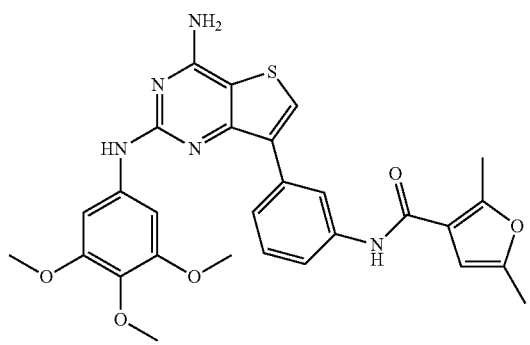

MS m/z: 545.96 [M+1].

Example 23

N-(3-(4-amino-2-(3,4,5-trimethoxyphenylamino)thieno[3,2-d]pyrimidin-7-yl)phenyl)benzo[b]thiophen-2-carboxamide

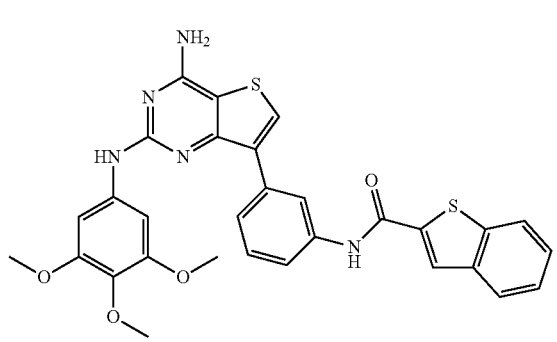 [SMILES: COc1cc(Nc2nc(N)c3scc(-c4cccc(NC(=O)c5cc6ccccc6s5)c4)c3n2)cc(OC)c1OC]

MS m/z: 583.90 [M+1].

Example 24

N-(3-(4-amino-2-(3,4,5-trimethoxyphenylamino)thieno[3,2-d]pyrimidin-7-yl)phenyl)-2-chloroisonicotinamide

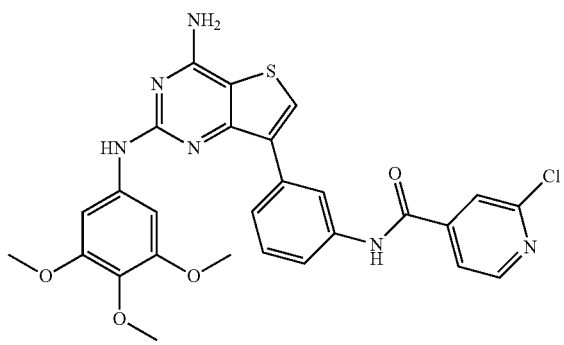 [SMILES: COc1cc(Nc2nc(N)c3scc(-c4cccc(NC(=O)c5ccnc(Cl)c5)c4)c3n2)cc(OC)c1OC]

MS m/z: 562.91 [M+1].

Example 25

N-(3-(4-amino-2-(3,4,5-trimethoxyphenylamino)thieno[3,2-d]pyrimidin-7-yl)phenyl)thiazol-4-carboxamide

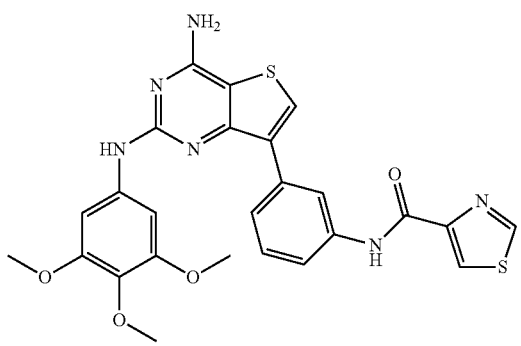 [SMILES: COc1cc(Nc2nc(N)c3scc(-c4cccc(NC(=O)c5cscn5)c4)c3n2)cc(OC)c1OC]

MS m/z: 534.91 [M+1].

Example 26

3-(4-amino-2-(3,4,5-trimethoxyphenylamino)thieno[3,2-d]pyrimidin-7-yl)-N-methylbenzenesulfonamide

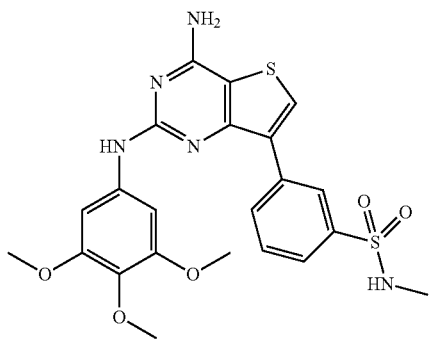

The compound of Example 26 represented by the above structural formula was prepared through the following 2-step process.

Step 1

3-(4-amino-2-chlorothieno[3,2-d]pyrimidin-7-yl)-N-methylbenzenesulfonamide

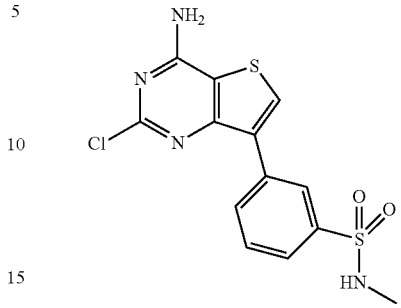

The target compound (480 mg, 71% yield) was prepared in the same manner as Step 1 of Example 11 using 7-bromo-2-chlorothieno[3,2-d]pyrimidin-4-amine (500 mg, 1.90 mmol) and 3-(N-methylsulfamoyl)phenylboronic acid (409 mg, 1.90 mmol).

$^1$H NMR (400 MHz, DMSO-$d_6$) δ 8.58 (s, 1H), 8.32 (s, 1H), 8.19 (d, 1H), 8.10 (s, 2H), 7.78 (d, 1H), 7.71 (t, 1H), 7.49 (m, 1H), 2.03 (s, 3H), MS m/z: 355.25 [M+1].

Step 2

3-(4-amino-2-(3,4,5-trimethoxyphenylamino)thieno[3,2-d]pyrimidin-7-yl)-N-methylbenzenesulfonamide The target compound of Example 26 (33 mg, 77% yield) was prepared in the same manner as Step 9 of Example 1 using 3-(4-amino-2-chlorothieno[3,2-d]pyrimidin-7-yl)-N-methylbenzenesulfonamide (30 mg, 0.085 mmol) and 3,4,5-trimethoxybenzenamine (31 mg, 0.170 mmol).

$^1$H NMR (400 MHz, DMSO-$d_6$) δ 8.73 (s, 1H), 8.36 (d, 1H), 8.26 (s, 1H), 8.11 (s, 1H), 7.75 (d, 1H), 7.67 (t, 1H), 7.46 (m, 1H), 7.23 (s, 2H), 7.16 (s, 2H), 3.58 (s, 6H), 3.56 (s, 3H), 2.40 (s, 3H), MS m/z: 502.37 [M+1].

Example 27

N-(3-(4-amino-2-(6-(4-ethylpiperazin-1-yl)pyridin-3-ylamino)thieno[3,2-d]pyrimidin-7-yl)phenyl)methanesulfonamide

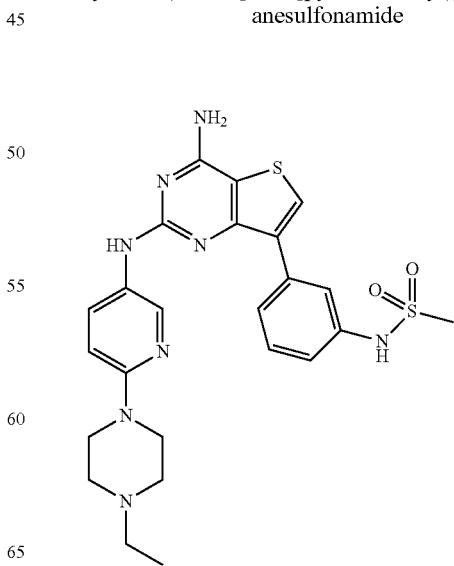

The compound of Example 27 represented by the above structural formula was prepared by a 3-step synthesis process as follows.

Step 1. 7-(3-aminophenyl)-2-chlorothieno[3,2-d]pyrimidin-4-amine

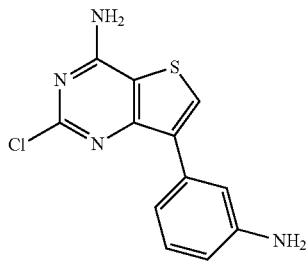 [SMILES: Nc1cccc(-c2csc3c(N)nc(Cl)nc23)c1]

The target compound (360 mg, 68% yield) was prepared in the same manner as Step 1 of Example 11 using 7-bromo-2-chlorothieno[3,2-d]pyrimidin-4-amine (500 mg, 1.90 mmol) and 3-aminophenylboronic acid (261 mg, 1.90 mmol).
MS m/z: 277.27 [M+1].

Step 2

N-(3-(4-amino-2-chlorothieno[3,2-d]pyrimidin-7-yl)phenyl)methanesulfonamide

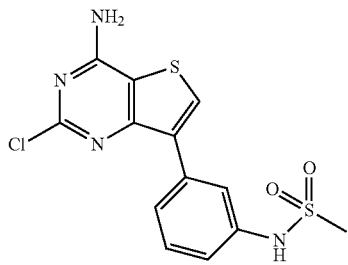 [SMILES: CS(=O)(=O)Nc1cccc(-c2csc3c(N)nc(Cl)nc23)c1]

The target compound (360 mg, 93% yield) was prepared in the same manner as the synthesis of the compound of Example 12, using 7-(3-aminophenyl)-2-chlorothieno[3,2-d]pyrimidin-4-amine (300 mg, 1.08 mmol) and methanesulfonyl chloride (94 μL, 1.19 mmol).
$^1$H NMR (400 MHz, DMSO-$d_6$) δ 9.90 (s, 1H), 8.31 (s, 1H), 8.06 (s, 1H), 7.78 (m, 1H), 7.62 (m, 2H), 7.45 (t, 1H), 7.19 (m, 1H), 3.09 (s, 3H), MS m/z: 355.25 [M+1].

Step 3

N-(3-(4-amino-2-(6-(4-ethylpiperazin-1-yl)pyridin-3-ylamino)thieno[3,2-d]pyrimidin-7-yl)phenyl)methanesulfonamide The target compound of Example 27 (22 mg, 74% yield) was prepared in the same manner as Step 9 of Example 1 using N-(3-(4-amino-2-chlorothieno[3,2-d]pyrimidin-7-yl)phenyl)methanesulfonamide (20 mg, 0.056 mmol) and 6-(4-ethylpiperazin-1-yl)pyridin-3-amine (31 mg, 0.17 mmol).
MS m/z: 525.04 [M+1].

Example 28

N-(3-(4-amino-2-(6-morpholinopyrimidin-4-ylamino)thieno[3,2-d]pyrimidin-7-yl)phenyl)methanesulfonamide

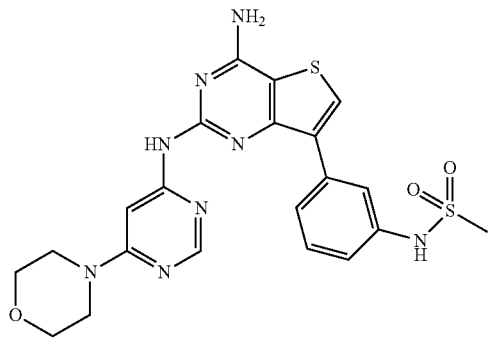 [SMILES: CS(=O)(=O)Nc1cccc(-c2csc3c(N)nc(Nc4cc(N5CCOCC5)ncn4)nc23)c1]

MS m/z: 499.00 [M+1].

Example 2

N-(3-(4-amino-2-(6-(4-ethylpiperazin-1-yl)pyrimidin-4-ylamino)thieno[3,2-d]pyrimidin-7-yl)phenyl)methanesulfonamide

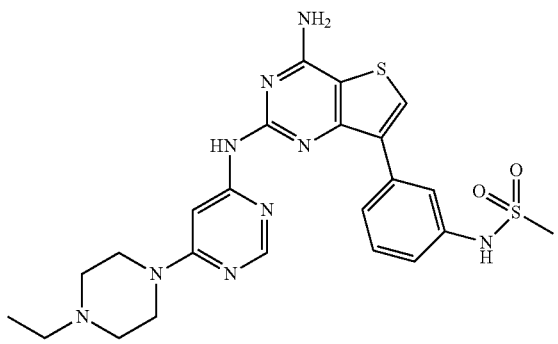 [SMILES: CCN1CCN(c2cc(Nc3nc(N)c4scc(-c5cccc(NS(C)(=O)=O)c5)c4n3)ncn2)CC1]

MS m/z: 526.03 [M+1].

Example 30

N-(3-(4-amino-2-(6-morpholinopyridin-3-ylamino)thieno[3,2-d]pyrimidin-7-yl)phenyl)methanesulfonamide

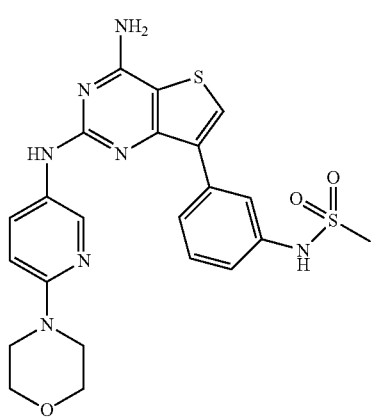 [SMILES: CS(=O)(=O)Nc1cccc(-c2csc3c(N)nc(Nc4ccc(N5CCOCC5)nc4)nc23)c1]

MS m/z: 498.00 [M+1].

Example 31

N-(3-(4-amino-2-(4-(4-hydroxypiperidin-1-yl)phenylamino)thieno[3,2-d]pyrimidin-7-yl)phenyl)methanesulfonamide

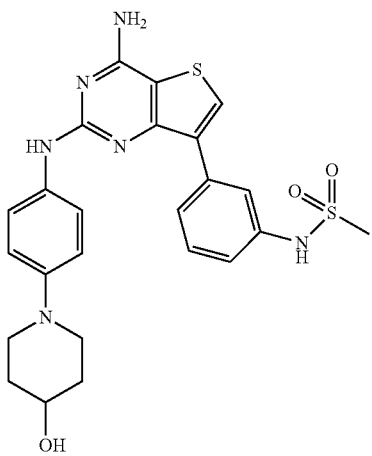 [SMILES: CS(=O)(=O)Nc1cccc(-c2csc3c(N)nc(Nc4ccc(N5CCC(O)CC5)cc4)nc23)c1]

MS m/z: 511.01 [M+1].

Example 32

N-(3-(4-amino-2-(4-(4-ethylpiperazin-1-yl)phenylamino)thieno[3,2-d]pyrimidin-7-yl)phenyl)methanesulfonamide

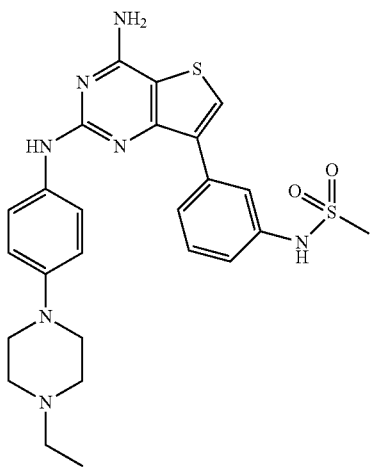 [SMILES: CCN1CCN(c2ccc(Nc3nc(N)c4scc(-c5cccc(NS(C)(=O)=O)c5)c4n3)cc2)CC1]

MS m/z: 524.06 [M+1].

Example 33

N-(3-(4-amino-2-(4-((4-ethylpiperazin-1-yl)methyl)phenylamine)thieno[3,2-d]pyrimidin-7-yl)phenyl)methanesulfonamide

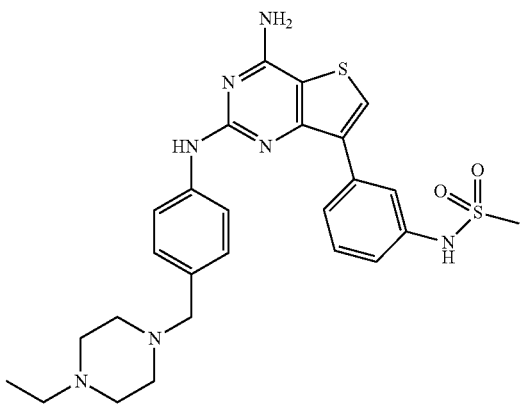 [SMILES: CCN1CCN(Cc2ccc(Nc3nc(N)c4scc(-c5cccc(NS(C)(=O)=O)c5)c4n3)cc2)CC1]

MS m/z: 538.06 [M+1].

Example 34

N-(3-(4-amino-2-(4-morpholinophenylamino)[3,2-d]pyrimidin-7-yl)phenyl)methanesulfonamide

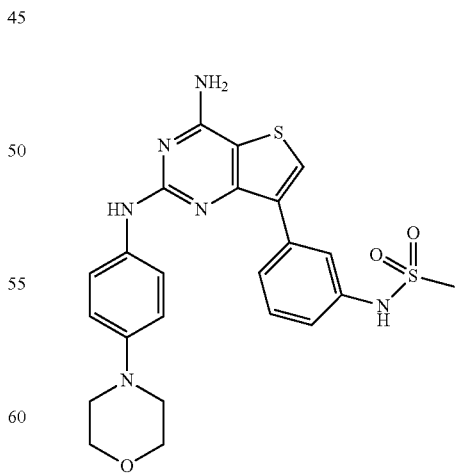

MS m/z: 497.00 [M+1].

Example 35

N-(3-(4-amino-2-(4-(2-(4-ethylpiperazin-1-yl)ethyl)
phenylamino)thieno[3,2-d]pyrimidin-7-yl)phenyl)
methanesulfonamide

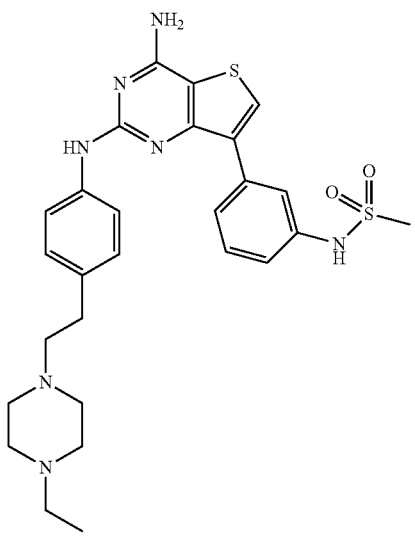 [SMILES: CCN1CCN(CCc2ccc(Nc3nc(N)c4scc(-c5cccc(NS(C)(=O)=O)c5)c4n3)cc2)CC1]

MS m/z: 552.08 [M+1].

Example 36

N-(3-(4-amino-2-(4-(4-(dimethylamino)piperidin-1-
yl)phenylamino)thieno[3,2-d]pyrimidin-7-yl)phenyl)
methanesulfonamide

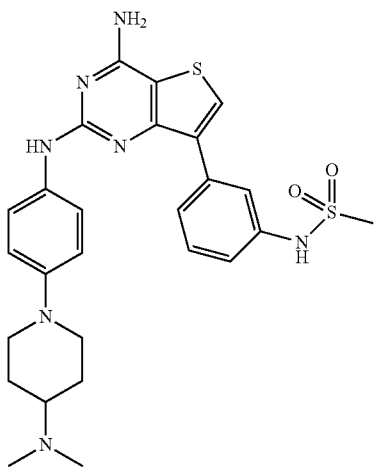 [SMILES: CN(C)C1CCN(c2ccc(Nc3nc(N)c4scc(-c5cccc(NS(C)(=O)=O)c5)c4n3)cc2)CC1]

MS m/z: 538.07 [M+1].

Example 37

N-(3-(4-amino-2-(3-(4-ethylpiperazin-1-yl)phe-
nylamino)thieno[3,2-d]pyrimidin-7-yl)phenyl)meth-
anesulfonamide

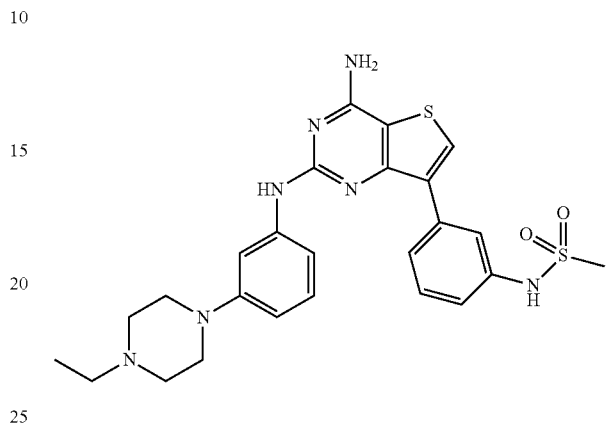

MS m/z: 524.06 [M+1].

Example 38

N-(3-(4-amino-2-(4-(4-(pyrrolidin-1-yl)piperidin-1-
yl)phenylamino)thieno[3,2-d]pyrimidin-7-yl)phenyl)
methanesulfonamide

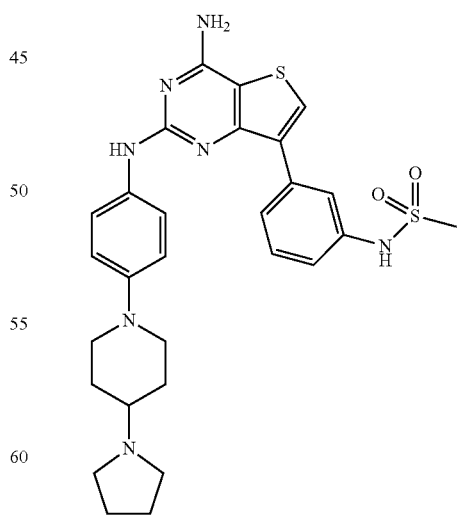

MS m/z: 564.06 [M+1].

Example 39

N²-(6-(4-ethylpiperazin-1-yl)pyridin-3-yl)-7-(quinolin-3-yl)thieno[3,2-d]pyrimidin-2,4-diamine

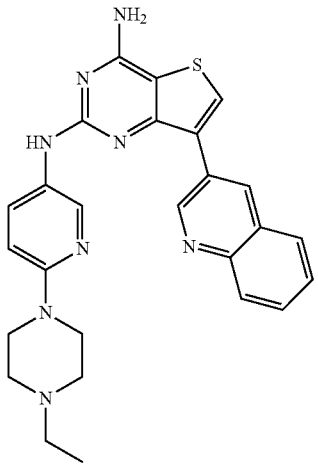 [SMILES: CCN1CCN(c2ccc(Nc3nc(N)c4scc(-c5cnc6ccccc6c5)c4n3)cn2)CC1]

The compound of Example 39 represented by the above structural formula was prepared by a 2-step synthesis process as follows.

Step 1. 2-chloro-7-(quinolin-3-yl)thieno[3,2-d]pyrimidin-4-amine

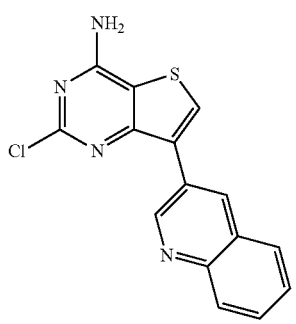 [SMILES: Nc1nc(Cl)nc2c(-c3cnc4ccccc4c3)csc12]

The target compound (260 mg, 43% yield) was prepared in the same manner as Step 1 of Example 11 using 7-bromo-2-chlorothieno[3,2-d]pyrimidin-4-amine (500 mg, 1.90 mmol) and quinolin-3-ylboronic acid (329 mg, 1.90 mmol).

Step 2

N²-(6-(4-ethylpiperazin-1-yl)pyridin-3-yl)-7-(quinolin-3-yl)thieno[3,2-d]pyrimidin-2,4-diamine The target compound of Example 30 (21 mg, 68% yield) was prepared in the same manner as Step 9 of Example 1 using 2-chloro-7-(quinolin-3-yl)thieno[3,2-d]pyrimidin-4-amine (20 mg, 0.064 mmol) and 6-(4-ethylpiperazin-1-yl)pyridin-3-amine (20 mg, 0.096 mmol).

MS m/z: 482.98 [M+1]

Example 40

N²-(4-morpholinophenyl)-7-(quinolin-3-yl)thieno[3,2-d]pyrimidin-2,4-diamine

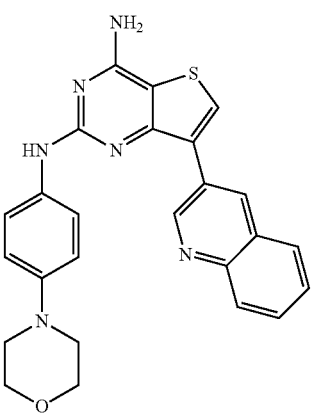 [SMILES: Nc1nc(Nc2ccc(N3CCOCC3)cc2)nc2c(-c3cnc4ccccc4c3)csc12]

MS m/z: 454.95 [M+1].

Example 41

N²-(4-(4-ethylpiperazin-1-yl)phenyl)-7-(quinolin-3-yl)thieno[3,2-d]pyrimidin-2,4-amine

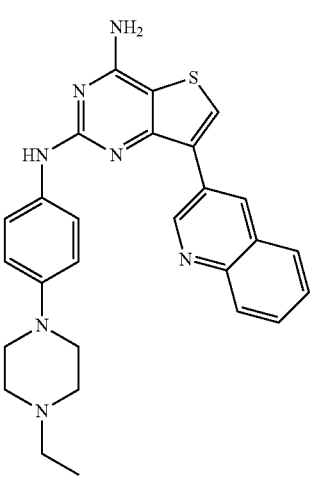 [SMILES: CCN1CCN(c2ccc(Nc3nc(N)c4scc(-c5cnc6ccccc6c5)c4n3)cc2)CC1]

MS m/z: 481.99 [M+1].

Example 42

N²-(6-morpholinopyridin-3-yl)-7-(quinolin-3-yl)thieno[3,2-d]pyrimidin-2,4-diamine

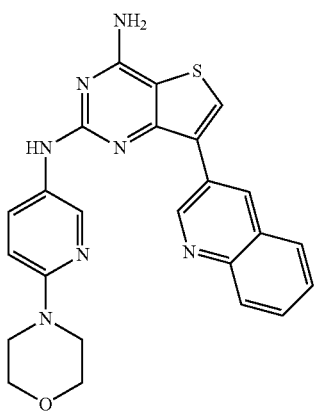 [SMILES: Nc1nc(Nc2ccc(N3CCOCC3)nc2)nc2c(-c3cnc4ccccc4c3)csc12]

MS m/z: 455.95 [M+1].

Example 43

N²-(3-(4-ethylpiperazin-1-yl)phenyl)-7-(quinolin-3-yl)thieno[3,2-d]pyrimidin-2,4-diamine

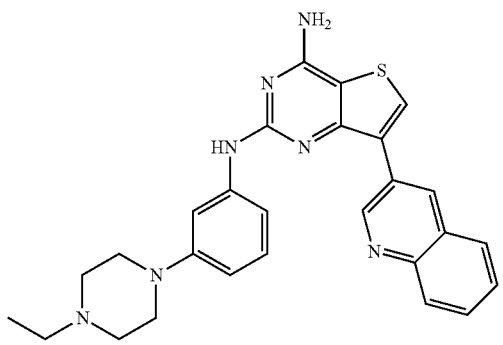 [SMILES: CCN1CCN(c2cccc(Nc3nc(N)c4scc(-c5cnc6ccccc6c5)c4n3)c2)CC1]

MS m/z: 481.99 [M+1].

Example 44

(S)-1-(4-(benzylamino)-7-ethynylthieno[3,2-d]pyrimidin-2-ylamino)propan-2-ol

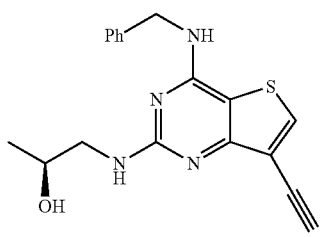 [SMILES: C#Cc1csc2c(NCc3ccccc3)nc(NC[C@H](C)O)nc12]

The compound of Example 44 represented by the above structural formula was prepared by a 3-step synthesis process as follows.

Step 1. N-benzyl-7-bromo-2-chlorothieno[3,2-d]pyrimidin-4-amine

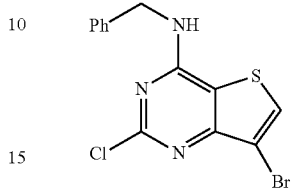

7-Bromo-2,4-dichlorothieno[3,2-d]pyrimidine (500 mg, 1.77 mmol) was dissolved in anhydrous tetrahydrofuran (8 mL) and stirred at 60° C. for 2 hours after adding benzylamine (0.58 mL, 5.32 mmol). The reaction mixture was cooled to room temperature and added to water (30 mL). Thus prepared solid was filtered and dried with nitrogen gas. The resultant target compound (580 mg, 92% yield) was used in the following reaction without purification.

Step 2. N-benzyl-2-chloro-7-ethynylthieno[3,2-d]pyrimidin-4-amine

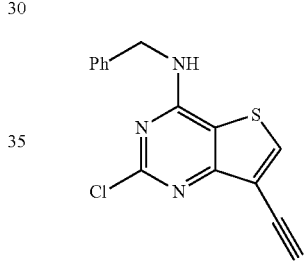

N-Benzyl-7-bromo-2-chlorothieno[3,2-d]pyrimidin-4-amine (310 mg, 0.874 mmol) was dissolved in acetonitrile (4 mL) and then bis(triphenylphosphine)palladium(II) dichloride (15 mg, 0.022 mmol), CuI (6 mg, 0.350 mmol), dicyclohexylamine (0.19 mL, 0.96 mmol) and ethynyltrimethylsilane (0.24 mL, 1.75 mmol) were added. After flowing nitrogen gas for 15 minutes, the reaction mixture was stirred at 80° C. for 14 hours. After cooling to room temperature, the reaction mixture was filtered with celite and washed with ethyl acetate (50 mL). The filtrate was washed with brine and concentrated by drying with MgSO₄. Without purification, the resultant compound was dissolved in anhydrous tetrahydrofuran (5 mL) and then 1.0 M tetrabutylammonium fluoride dissolved in tetrahydrofuran (4.4 mL, 4.4 mmol) was added thereto. The reaction mixture was stirred at room temperature for 30 minutes and then concentrated. Purification of the mixture by silica gel chromatography (ethyl acetate/hexane: 2/8→3/7) yielded the target compound (180 mg, 68% yield).

Step 3

(S)-1-(4-(benzylamino)-7-ethynylthieno[3,2-d]pyrimidin-2-ylamino)propan-2-ol

N-Benzyl-2-chloro-7-ethynylthieno[3,2-d]pyrimidin-4-amine (30 mg, 0.096 mmol) was dissolved in anhydrous dioxane (0.5 mL) and (S)-1-aminopropan-2-ol (23 μL, 0.288 mmol) was added. The reaction mixture was stirred at 120° C. for 24 hours. After adding ethyl acetate (3 mL), the reaction mixture was washed with brine. After drying with MgSO₄ and concentrating by filtration, purification by silica gel chromatography (ethyl acetate/hexane:1/3→1/1) yielded the target compound of Example 44 (17 mg, 50% yield).

MS m/z: 339.32 [M+1].

Example 4

(S)-1-(7-ethynyl-4-((R)-1-phenylethylamino)thieno[3,2-d]pyrimidin-2-ylamino)propan-2-ol

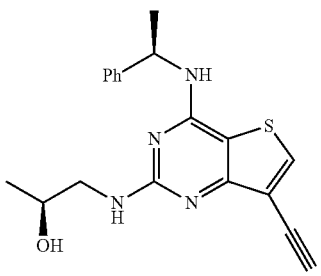 [SMILES: C#Cc1csc2c(N[C@H](C)c3ccccc3)nc(NC[C@H](C)O)nc12]

The compound of Example 45 represented by the above structural formula was prepared by a 3-step synthesis process as follows.

Step 1. (R)-7-bromo-2-chloro-N-(1-phenylethyl)thieno[3,2-d]pyrimidin-4-amine

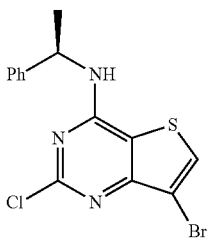 [SMILES: C[C@@H](Nc1nc(Cl)nc2c(Br)csc12)c1ccccc1]

The target compound (540 mg, 83% yield) was prepared in the same manner as Step 1 of Example 44 using 7-bromo-2,4-dichlorothieno[3,2-d]pyrimidine (500 mg, 1.77 mmol) and (R)-1-phenylethanamine (0.68 mL, 5.31 mmol).

Step 2. (R)-2-chloro-7-ethynyl-N-(1-phenylethyl)thieno[3,2-d]pyrimidin-4-amine

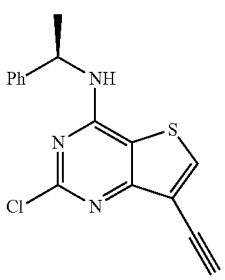 [SMILES: C#Cc1csc2c(N[C@H](C)c3ccccc3)nc(Cl)nc12]

The target compound (180 mg, 65% yield) was prepared in the same manner as Step 2 of Example 44 using (R)-7-bromo-2-chloro-N-(1-phenylethyl)thieno[3,2-d]pyrimidin-4-amine (325 mg, 0.88 mmol).

Step 3

(S)-1-(7-ethynyl-4-((R)-1-phenylethylamino)thieno[3,2-d]pyrimidin-2-ylamino)propan-2-ol The target compound of Example 45 (23 mg, 68% yield) was prepared in the same manner as Step 3 of Example 44 using (R)-2-chloro-7-ethynyl-N-(1-phenylethyl)thieno[3,2-d]pyrimidin-4-amine (30 mg, 0.092 mmol).

MS m/z: 353.02 [M+1].

Example 46

$N^4$-benzyl-$N^2$-(2-morpholinoethyl)-7-vinylthieno[3,2-d]pyrimidin-2,4-diamine

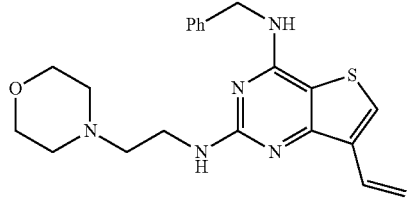 [SMILES: C=Cc1csc2c(NCc3ccccc3)nc(NCCN3CCOCC3)nc12]

The compound of Example 46 represented by the above structural formula was prepared by a 3-step synthesis process as follows.

Step 1. N-benzyl-2-chloro-7-vinylthieno[3,2-d]pyrimidin-4-amine

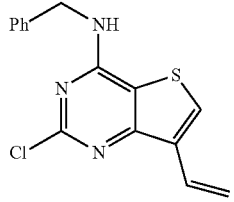 [SMILES: C=Cc1csc2c(NCc3ccccc3)nc(Cl)nc12]

N-Benzyl-7-bromo-2-chlorothieno[3,2-d]pyrimidin-4-amine (200 mg, 0.56 mmol) was dissolved in dioxane (2.5 mL) and nitrogen was flown for 20 minutes. After adding Pd(PPh₃)₄ (41 mg, 0.036 mmol) and tributyl(vinyl)tin (0.18 mL, 0.62 mmol), the mixture was stirred at 120° C. for 7 hours. The reaction mixture was cooled to room temperature and stirred for 2 hours after adding 10% potassium fluoride aqueous solution (5 mL). The reaction solution was filtered with celite and washed with ethyl acetate. The aqueous layer was separated from the organic layer and extracted once more with ethyl acetate. The combined organic layer was concentrated by drying with MgSO₄. Purification of the mixture by silica gel chromatography (DCM/MeOH=97/3) yielded the target compound (95 mg, 55% yield).

Step 2

N⁴-benzyl-N²-(2-morpholinoethyl)-7-vinylthieno[3,2-d]pyrimidin-2,4-diamine

The target compound of Example 46 (36 mg, 78% yield) was prepared in the same manner as Step 3 of Example 44 using N-benzyl-2-chloro-7-vinylthieno[3,2-d]pyrimidin-4-amine (35 mg, 0.116 mmol) and 2-morpholinoethanamine (75 mg, 0.58 mmol).
MS m/z: 396.03 [M+1].

Example 47

(R)—N²-(2-morpholinoethyl)-N⁴-(1-phenylethyl)-7-vinylthieno[3,2-d]pyrimidin-2,4-diamine

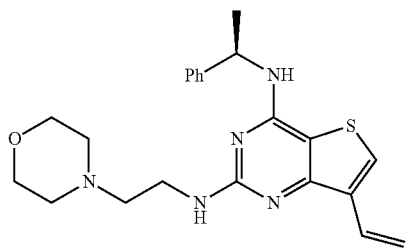 [SMILES: C=Cc1csc2c(N[C@H](C)c3ccccc3)nc(NCCN3CCOCC3)nc12]

The compound of Example 47 represented by the above structural formula was prepared by a 2-step synthesis process as follows.

Step 1. (R)-2-chloro-N-(1-phenylethyl)-7-vinylthieno[3,2-d]pyrimidin-4-amine

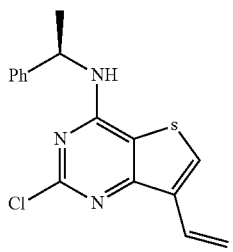

The target compound (84 mg, 49% yield) was prepared in the same manner as Step 1 of Example 46 using (R)-7-bromo-2-chloro-N-(1-phenylethyl)thieno[3,2-d]pyrimidin-4-amine (200 mg, 0.54 mmol).

Step 2

(R)—N²-(2-morpholinoethyl)-N⁴-(1-phenylethyl)-7-vinylthieno[3,2-d]pyrimidin-2,4-diamine The target compound of Example 47 (34 mg, 65% yield) was prepared in the same manner as Step 3 of Example 44 using (R)-2-chloro-N-(1-phenylethyl)-7-vinylthieno[3,2-d]pyrimidin-4-amine (40 mg, 0.127 mmol) and 2-morpholinoethanamine (82 mg, 0.63 mmol).
MS m/z: 410.03 [M+1].

Example 48

N⁴-benzyl-7-ethyl-N²-(2-morpholinoethyl)thieno[3,2-d]pyrimidin-2,4-diamine

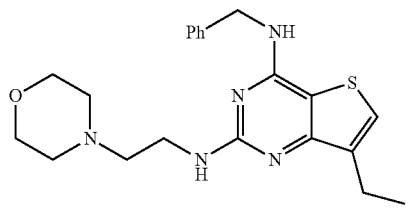 [SMILES: CCc1csc2c(NCc3ccccc3)nc(NCCN3CCOCC3)nc12]

Raney Ni was added to (R)—N²-(2-Morpholinoethyl)-N⁴-(1-phenylethyl)-7-vinylthieno[3,2-d]pyrimidin-2,4-diamine (10 mg, 0.025 mmol) in methanol (1 mL), and the mixture was stirred at room temperature for 24 hours under a pressure of a balloon filled with hydrogen gas. Filtration of the reaction mixture with celite followed by washing with methanol and concentration yielded the target compound (9 mg, 89% yield).
MS m/z: 398.03 [M+1].

Example 49 is an example of preparing a pharmaceutically acceptable salt of the compound represented by Chemical Formula 1. However, the scope of the present invention is not limited by the specific example.

Example 49

3-(4-amino-2-(6-(4-ethylpiperazin-1-yl)pyridin-3-ylamino)thieno[3,2-d]pyrimidin-7-yl)-N-methylbenzamide hydrochloride

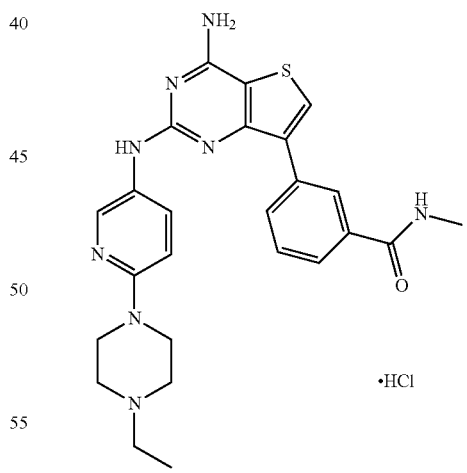

3-(4-Amino-2-(6-(4-ethylpiperazin-1-yl)pyridin-3-ylamino)thieno[3,2-d]pyrimidin-7-yl)-N-methylbenzamide (300 mg, 0.615 mmol) was dissolved in tetrahydrofuran (5 mL) and then 4 M hydrogen chloride (169 μL) dissolved in dioxane was added at room temperature. 5 hours later, thus prepared precipitate was filtered and dried at room temperature. The target compound 3-(4-amino-2-(6-(4-ethylpiperazin-1-yl)pyridin-3-ylamino)thieno[3,2-d]pyrimidin-7-yl)-N-methylbenzamide hydrochloride (295 mg) was yielded.

The novel compound represented by Chemical Formula 1 may be prepared into various formulations depending on purposes. The following examples illustrate some formulation comprising the compound represented by Chemical Formula 1 as an active ingredient, but they do not limit the present invention.

FORMULATION EXAMPLES

Formulation Example 1

Tablet (Direct Compression)

The active ingredient (5.0 mg) was sieved, mixed with lactose (14.1 mg), crospovidone USNF (0.8 mg) and magnesium stearate (0.1 mg), and then compressed into a tablet.

Formulation Example 2

Tablet (Wet Granulation)

The active ingredient (5.0 mg) was sieved and mixed with lactose (16.0 mg) and starch (4.0 mg). An adequate amount of the resulting solution was added to Polysorbate 80 (0.3 mg) dissolved in pure water, and then formed into granules. After drying, the granules were sieved and mixed with colloidal silicon dioxide (2.7 mg) and magnesium stearate (2.0 mg). The granules were compressed into a tablet.

Formulation Example 3

Powder and Capsule

The active ingredient (5.0 mg) was sieved and mixed with lactose (14.8 mg), polyvinylpyrrolidone (10.0 mg) and magnesium stearate (0.2 mg). The mixture was filled in a hard No. 5 gelatin capsule using an adequate apparatus.

Formulation Example 4

Injection

The active ingredient (100 mg) was mixed with mannitol (180 mg), $Na_2HPO_4 \cdot 12H_2O$ (26 mg) and distilled water (2974 mg) to prepare an injection.

TEST EXAMPLES

Test Example 1

Measurement of FAK Kinase Activity
(ULight-LANCE Assay)

Full sequence FAK was purchased from Cell Signaling (Catalog No.: 7796). ULight-poly GT (PerkinElmer #TRF0100-D), Eu-anti-phospho-Tyr (PT66) (PerkinElmer #AD0068) and Lance detection buffer (PerkinElmer #CR-97-100) were purchased from PerkinElmer. The kinase solution (50 mM Tris-HCl pH 7.5, 10 mM $MgCl_2$, 1 mM EGTA, 2 mM DTT, 0.01% Tween-20) was adjusted to a final concentration of 3 nM by adding FAK diluted to 6 nM (2×) in white 384 OptiPlate, and added with an amount of 5 µL. 4× ULight-poly GT was adjusted to a final concentration of 100 nM. ATP (Sigma #A2383) was adjusted to a final concentration of 10 µM and in 2.5 µL aliquots. The test compound was sequentially diluted at 12 concentrations and treated with an amount of 0.5 µL. After shaking well and allowing to react at room temperature for 60 minutes, 5 µL of ethylenediaminetetraacetic acid (EDTA, final concentration 40 mM) diluted in Lance detection buffer (Lance detection buffer) was added and the mixture was left at room temperature for 5 minutes to stop the reaction. After adding 4× Eu-anti-phospho-Tyr (PT66) phosphorylated antibody diluted to a final concentration of 2 nM in detection buffer with an amount of 5 µL, and reaction was performed at room temperature for 60 minutes. After adjusting to detect time-resolved fluorescence energy transfer (TR-FRET) at excitation wavelength 320 nm and emission wavelength 665 nm, signals were detected using EnVision Multilabel Reader.

The FAK inhibition activity of the compound represented by Chemical Formula 1 was measured. $IC_{50}$ ranged from 0.025 µM to 20 µM. FAK inhibition activity of some typical compounds according to the present invention is given in Table 1

TABLE 1

| Test compounds | FAK inhibition activity ($IC_{50}$, µM) |
| --- | --- |
| Example 2 | <10 |
| Example 3 | <10 |
| Example 6 | <10 |
| Example 7 | <10 |
| Example 15 | <10 |
| Example 17 | <10 |
| Example 26 | <10 |
| Example 27 | <10 |
| Example 39 | <10 |
| Example 41 | <10 |
| Example 42 | <10 |
| Example 43 | <10 |
| Example 44 | <10 |
| Example 45 | <10 |
| Example 46 | <10 |
| Example 47 | <10 |
| Example 48 | <10 |

Test Example 2

Measurement of Inhibition Activity Against Proliferation of HT-29 Human Colon Adenocarcinoma Cells HT-29 human colon adenocarcinoma cells were cultured in DMEM [10% FBS, 1% penicillin/streptomycin] at 37° C. in the presence of 5% $CO_2$. The cultured HT-29 cells were harvested with 0.05% trypsin-0.02% EDTA and seeded in a 96-well plate at $5 \times 10^3$ cells per well.

3-(4,5-Dimethylthiazol-2-yl)-2,5-diphenyltetrazolium bromide (MTT) assay (CellTiter 96 Assay, Promega) was used to measure cell viability. After adding 15 µL of a dye per well and culturing for 2 hours, the cells were treated with 100 µL of a stop solution and absorbance was measured 24 hours later. The test compound was treated a day after plating. The test compound had been sequentially diluted at 12 concentrations from a 10 mM stock solution using sterilized dimethylsulfoxide (DMSO) and treated with an amount of 0.5 µL. Absorbance at 590 nm was recorded using EnVision2103, and $GI_{50}$ value was calculated using Graph-Pad Prism 4.0 software.

The compounds represented by Chemical Formula 1 exhibited inhibition activity against proliferation of the HT-29 human colon adenocarcinoma cells. $GI_{50}$ ranged from 0.1 µM to 20 µM. The inhibition activity against proliferation of the HT-29 human colon adenocarcinoma cells of some typical compounds according to the present invention is given in Table 2.

TABLE 2

| Test compounds | Inhibition activity against proliferation of the HT-29 cells (GI$_{50}$, μM) |
| --- | --- |
| Example 2 | <10 |
| Example 3 | <10 |
| Example 6 | <10 |
| Example 7 | <10 |
| Example 15 | <10 |
| Example 17 | <10 |
| Example 26 | <10 |
| Example 27 | <10 |
| Example 39 | <10 |
| Example 41 | <10 |
| Example 42 | <10 |
| Example 43 | <10 |
| Example 44 | <10 |
| Example 45 | <10 |
| Example 46 | <10 |
| Example 47 | <10 |
| Example 48 | <10 |

INDUSTRIAL APPLICABILITY

As described, since the 2,4,7-substituted thieno[3,2-d]pyrimidine compound represented by Chemical Formula 1 or a pharmaceutically acceptable exhibits inhibition activity against protein kinases, it is useful for preventing and treating cancers caused by abnormal cell growth induced by protein kinases, such as cancers selected from stomach cancer, lung cancer, liver cancer, colorectal cancer, small intestine cancer, pancreatic cancer, brain cancer, bone cancer, melanoma, breast cancer, sclerosing adenoma, uterine cancer, cervical cancer, head and neck cancer, esophageal cancer, thyroid cancer, parathyroid cancer, renal cancer, sarcoma, prostate cancer, urethral cancer, bladder cancer, leukemia, multiple myeloma, hematological malignancy such as myelodysplastic syndrome, lymphoma such as Hodgkin's disease and non-Hodgkin lymphoma and fibroadenoma.

The present application contains subject matter related to Korean Patent Application No. 10-2009-0112132, filed in the Korean Intellectual Property Office on Nov. 19, 2009, the entire contents of which is incorporated herein by reference.

While the present invention has been described with respect to the specific embodiments, it will be apparent to those skilled in the art that various changes and modifications may be made without departing from the spirit and scope of the invention as defined in the following claims.

The invention claimed is:

1. A 2,4,7-substituted thieno[3,2-d]pyrimidine compound represented by Chemical Formula 1, a pharmaceutically acceptable salt thereof, a hydrate thereof or a solvate thereof:

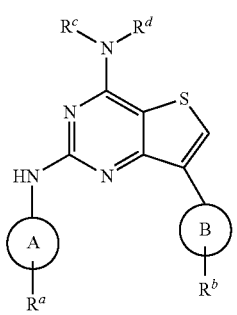

Chemical Formula 1 wherein
A represents hydroxyC$_1$-C$_6$ alkyl, morpholinoC$_1$-C$_6$ alkyl, phenyl, pyridinyl or pyrimidinyl;
R$^a$ represents hydrogen, C$_1$-C$_6$ alkyl, C$_1$-C$_6$ alkoxy, morpholino, piperidinyl substituted or unsubstituted with a substituent selected from hydroxy, C$_1$-C$_6$ alkyl, amino, C$_1$-C$_6$ alkylamino, di(C$_1$-C$_6$ alkyl)amino and pyrrolidinyl, or piperazinyl substituted or unsubstituted with a substituent selected from hydroxy and C$_1$-C$_6$ alkyl;
B represents C$_1$-C$_6$ alkyl, C$_2$-C$_6$ alkenyl, C$_2$-C$_6$ alkynyl, phenyl or quinolinyl;
R$^b$ represents hydrogen, —C(O)NR$^1$R$^2$, —NR$^3$C(O)R$^1$, —NR$^2$C(O)NR$^1$R$^2$, —SO$_2$NR$^1$R$^2$ or —NR$^3$SO$_2$R$^1$;
R$^c$ and R$^d$, which are the same or different, represent hydrogen, C$_1$-C$_6$ alkyl or —(CH$_2$)$_n$-phenyl;
R$^1$ and R$^2$, which are the same or different, represent hydrogen, C$_1$-C$_6$ alkyl, C$_1$-C$_6$ haloalkyl, —(CH$_2$)$_n$-phenyl, or 5- to 12-membered single or fused heteroaryl containing 1 to 4 heteroatom(s) selected from oxygen, nitrogen and sulfur atoms, wherein the phenyl or the heteroaryl is substituted or unsubstituted with a substituent selected from halo, C$_1$-C$_6$ haloalkyl, C$_1$-C$_6$ alkyl and C$_1$-C$_6$ alkoxy;
R$^3$ represents hydrogen or C$_1$-C$_6$ alkyl; and
n represents an integer from 0 to 3.

2. The compound according to claim 1, which is selected from the group consisting of:
3-(4-amino-2-(6-(4-ethylpiperazin-1-yl)pyridin-3-ylamino)thieno[3,2-d]pyrimidin-7-yl)-N-methylbenzamide;
3-(4-amino-2-(6-morpholinopyridin-3-ylamino)thieno[3,2-d]pyrimidin-7-yl)-N-methylbenzamide;
3-(4-amino-2-(4-(4-hydroxypiperidin-1-yl)phenylamino)thieno[3,2-d]pyrimidin-7-yl)-N-methylbenzamide;
3-(4-amino-2-(4-(1-ethylpiperidin-4-yl)phenylamino)thieno[3,2-d]pyrimidin-7-yl)-N-methylbenzamide;
3-(4-amino-2-(3-(4-ethylpiperazin-1-yl)phenylamino)thieno[3,2-d]pyrimidin-7-yl)-N-methylbenzamide;
3-(4-amino-2-(4-(4-ethylpiperazin-1-yl)phenylamino)thieno[3,2-d]pyrimidin-7-yl)-N-methylbenzamide;
3-(4-amino-2-(4-(4-(pyrrolidin-1-yl)piperidin-1-yl)phenylamino)thieno[3,2-d]pyrimidin-7-yl)-N-methylbenzamide;
3-(4-amino-2-(6-morpholinopyrimidin-4-ylamino)thieno[3,2-d]pyrimidin-7-yl)-N-methylbenzamide;
3-(4-amino-2-(6-(4-ethylpiperazin-1-yl)pyrimidin-4-ylamino)thieno[3,2-d]pyrimidin-7-yl)-N-methylbenzamide;
3-(4-amino-2-(2-methoxy-4-morpholinophenylamino)thieno[3,2-d]pyrimidin-7-yl)-N-methylbenzamide;
7-(3-aminophenyl)-N$^2$-(3,4,5-trimethoxyphenyl)thieno[3,2-d]pyrimidin-2,4-diamine;
1-(3-(4-amino-2-(3,4,5-trimethoxyphenylamino)thieno[3,2-d]pyrimidin-7-yl)phenyl)-3-isopropylurea;
N-(3-(4-amino-2-(3,4,5-trimethoxyphenylamino)thieno[3,2-d]pyrimidin-7-yl)phenyl)methanesulfonamide;
1-(3-(4-amino-2-(3,4,5-trimethoxyphenylamino)thieno[3,2-d]pyrimidin-7-yl)phenyl)-3-(4-chloro-3-(trifluoromethyl)phenyl)urea;
N-(3-(4-amino-2-(3,4,5-trimethoxyphenylamino)thieno[3,2-d]pyrimidin-7-yl)phenyl)cyclopropanecarboxamide;
N-(3-(4-amino-2-(3,4,5-trimethoxyphenylamino)thieno[3,2-d]pyrimidin-7-yl)phenyl)acetamide;

N-(3-(4-amino-2-(3,4,5-trimethoxyphenylamino)thieno[3,2-d]pyrimidin-7-yl)phenyl)ethanesulfonamide;
1-(3-(4-amino-2-(3,4,5-trimethoxyphenylamino)thieno[3,2-d]pyrimidin-7-yl)phenyl)-3-butylurea;
N-(3-(4-amino-2-(3,4,5-trimethoxyphenylamino)thieno[3,2-d]pyrimidin-7-yl)phenyl)-2-(3,4-dimethoxyphenyl)acetamide;
N-(3-(4-amino-2-(3,4,5-trimethoxyphenylamino)thieno[3,2-d]pyrimidin-7-yl)phenyl)pyrazin-2-carboxamide;
N-(3-(4-amino-2-(3,4,5-trimethoxyphenylamino)thieno[3,2-d]pyrimidin-7-yl)phenyl)quinolin-6-carboxamide;
N-(3-(4-amino-2-(3,4,5-trimethoxyphenylamino)thieno[3,2-d]pyrimidin-7-yl)phenyl)-2, 5-dimethylfuran-3-carboxamide;
N-(3-(4-amino-2-(3,4,5-trimethoxyphenylamino)thieno[3,2-d]pyrimidin-7-yl)phenyl)benzo[b]thiophen-2-carboxamide;
N-(3-(4-amino-2-(3,4,5-trimethoxyphenylamino)thieno[3,2-d]pyrimidin-7-yl)phenyl)-2-chloroisonicotinamide;
N-(3-(4-amino-2-(3,4,5-trimethoxyphenylamino)thieno[3,2-d]pyrimidin-7-yl)phenyl)thiazol-4-carboxamide;
3-(4-amino-2-(3,4,5-trimethoxyphenylamino)thieno[3,2-d]pyrimidin-7-yl)-N-methylbenzenesulfonamide;
N-(3-(4-amino-2-(6-(4-ethylpiperazin-1-yl)pyridin-3-ylamino)thieno[3,2-d]pyrimidin-7-yl)pheny)methanesulfonamide;
N-(3-(4-amino-2-(6-morpholinopyrimidin-4-ylamino)thieno[3,2-d]pyrimidin-7-yl)phenyl)methanesulfonamide;
N-(3-(4-amino-2-(6-(4-ethylpiperazin-1-yl)pyrimidin-4-ylamino)thieno[3,2-d]pyrimidin-7-yl)phenyl)methanesulfonamide;
N-(3-(4-amino-2-(6-morpholinopyridin-3-ylamino)thieno[3,2-d]pyrimidin-7-yl)phenyl)methanesulfonamide;
N-(3-(4-amino-2-(4-(4-hydroxypiperidin-1-yl)phenylamino)thieno[3,2-d]pyrimidin-7-yl)phenyl)methanesulfonamide;
N-(3-(4-amino-2-(4-(4-ethylpiperazin-1-yl)phenylamino)thieno[3,2-d]pyrimidin-7-yl)phenyl)methanesulfonamide;
N-(3-(4-amino-2-(4-((4-ethylpiperazin-1-yl)methyl)phenylamino)thieno[3,2-d]pyrimidin-7-yl)phenyl)methanesulfonamide;
N-(3-(4-amino-2-(4-morpholinophenylamino[3,2-d]pyrimidin-7-yl)phenyl)methanesulfonamide;
N-(3-(4-amino-2-(4-(2-(4-ethylpiperazin-1-yl)ethyl)phenylamino)thieno[3,2-d]pyrimidin-7-yl)phenyl)methanesulfonamide;
N-(3-(4-amino-2-(4-(4-(dimethylamino)piperidin-1-yl)phenylamino)thieno[3,2-d]pyrimidin-7-yl)phenyl)methanesulfonamide;
N-(3-(4-amino-2-(3-(4-ethylpiperazin-1-yl)phenylamino)thieno[3,2-d]pyrimidin-7-yl)phenyl)methanesulfonamide;
N-(3-(4-amino-2-(4-(4-(pyrrolidin-1-yl)piperidin-1-yl)phenylamino)thieno[3,2-d]pyrimidin-7-yl)phenyl)methanesulfonamide;
$N^2$-(6-(4-ethylpiperazin-1-yl)pyridin-3-yl)-7-(quinolin-3-yl)thieno[3,2-d]pyrimidine-2,4-diamine;
$N^2$-(4-morpholinophenyl)-7-(quinolin-3-yl)thieno[3,2-d]pyrimidine-2,4-diamine;
$N^2$-(4-(4-ethylpiperazin-1-yl)phenyl)-7-(quinolin-3-yl)thieno[3,2-d]ipyrimidin-2,4-amine;
$N^2$-(6-morpholinopyridin-3-yl)-7-(quinolin-3-yl)thieno[3,2-d]oyrimidin-2,4-diamine;
$N^2$-(3-(4-ethylpiperazin-1-yl)phenyl)-7-(quinolin-3-yl)thieno[3,2-d]ipyrimidin-2,4-diamine;
(S)-1-(4-(benzylamino)-7-ethynylthieno[3,2-d]pyrimidin-2-ylamino)propan-2-ol;
(S)-1-(7-ethynyl-4-((R)-1-phenyl ethyl amino)thieno[3,2-d]pyrimidin-2-ylamino)propan-2-ol;
$N^4$-benzyl-$N^2$-(2-morpholinoethyl)-7-vinylthieno[3,2-d]pyrimidin-2,4-diamine;
(R)—$N^2$-(2-morpholinoethyl)-$N^4$-(1-phenylethyl)-7-vinylthieno[3,2-d]pyrimidin-2,4-diamine;
$N^4$-benzyl-7-ethyl-$N^2$-(2-morpholinoethyl)thieno[3,2-d]pyrimidin-2,4-diamine; and
3-(4-amino-2-(6-(4-ethylpiperazin-1-yl)pyridin-3-ylamino)thieno[3,2-d]pyrimidin-7-yl)-N-methylbenzamide hydrochloride.

3. A pharmaceutical composition comprising the compound according to claim 1 or 2 as an effective ingredient.

4. A method of treating colorectal cancer comprising administering to a patient a pharmaceutical composition of claim 3, wherein said cancer is treated by inhibiting a protein kinase, FAK.

5. An agent comprising the compound according to claim 1 or 2 as an effective ingredient.

6. A method for preparing a 2,4,7-substituted thieno[3,2-d]pyrimidine compound represented by Chemical Formula 1a, comprising:
subjecting a 7-bromo-2-chlorothieno[3,2-d]pyrimidin-4-amine compound represented by Chemical Formula 2 to Suzuki coupling reaction with a boronic acid compound represented by Chemical Formula 3a to prepare a compound represented by Chemical Formula 4a with a group B introduced at the C-7 position:

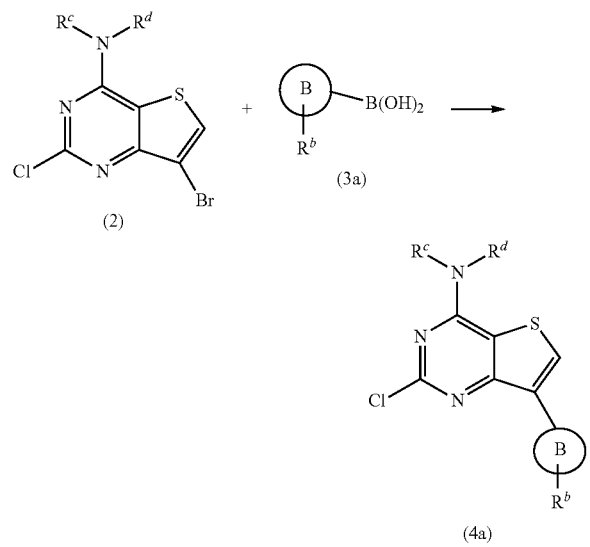

(wherein $R^c$ and $R^d$ are the same as defined in claim 1 and

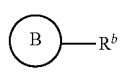

represents phenyl or quinolinyl); and
subjecting the compound represented by Chemical Formula 4a to Buchwald amination reaction with an amine compound represented by Chemical Formula 5 to prepare the compound represented by Chemical Formula 1a:

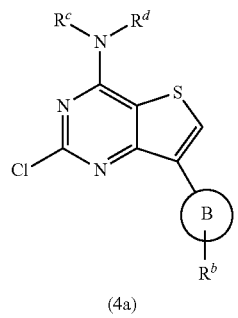 + 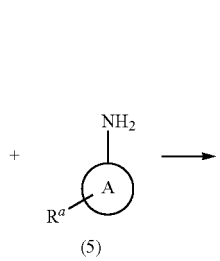 →

(4a)

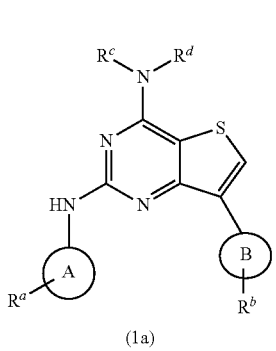

(1a)

(wherein A, $R^a$, $R^c$ and $R^d$ are the same as defined in claim 1 and

represents phenyl or quinolinyl).

7. A method for preparing a 2,4,7-substituted thieno[3,2-d]pyrimidine compound represented by Chemical Formula 1b, comprising:

subjecting a 7-bromo-2-chlorothieno[3,2-d]pyrimidin-4-amine compound represented by Chemical Formula 2 to Stille coupling reaction with tributyl(vinyl)tin to prepare a compound represented by Chemical Formula 4b with a vinyl group introduced at the C-7 position:

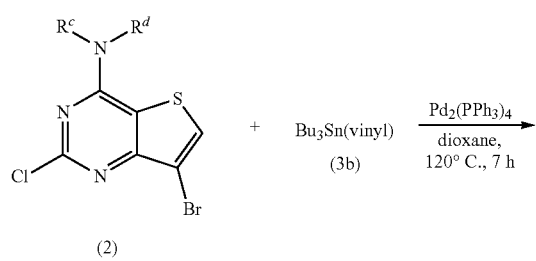

(2)

-continued

(4b)

(wherein $R^c$ and $R^d$ are the same as defined in claim 1); and subjecting the compound represented by Chemical Formula 4b to a coupling reaction with an amine compound represented by Chemical Formula 5 to prepare the compound represented by Chemical Formula 1b:

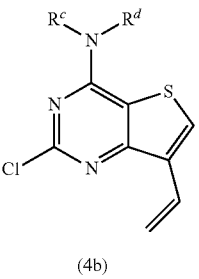 + 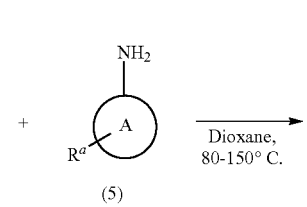

(4b)            (5)

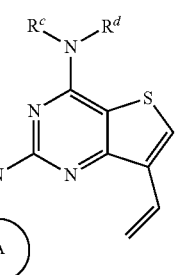

(1b)

(wherein A, $R^a$ $R^c$ and $R^d$ are the same as defined in claim 1).

8. A method for preparing a 2,4,7-substituted thieno[3,2-d]pyrimidine compound represented by Chemical Formula 1 c, comprising:

subjecting a 7-bromo-2-chloro-thieno[3,2-d]pyrimidin-4-amine compound represented by Chemical Formula 2 to Sonogashira reaction with ethynyltrimethylsilane to introduce a trimethylsilylethynyl group at the C-7 position, and reacting the product by stirring at room temperature in the presence of tetrabutylammonium fluoride (TBAF) to remove the trimethylsilyl (TMS) group, so as to prepare a compound represented by Chemical Formula 4c with an ethynyl group introduced at the C-7 position:

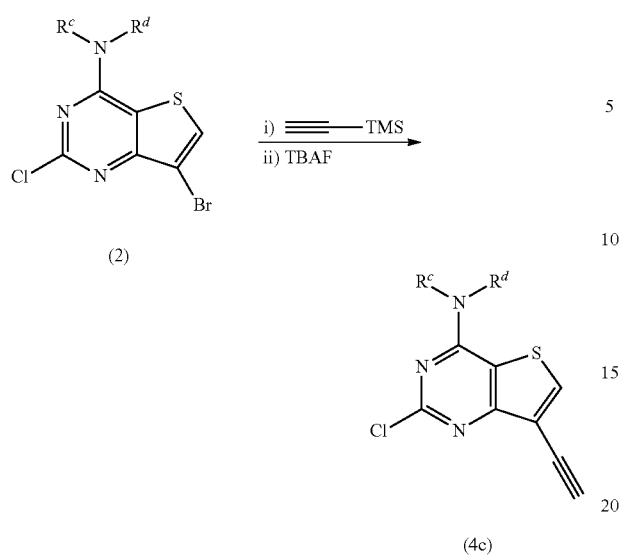

(2)

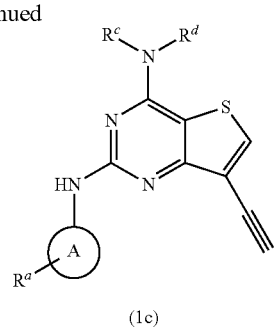

(4c)

(wherein $R^c$ and $R^d$ are the same as defined in claim 1); and subjecting the compound represented by Chemical Formula 4c to a coupling reaction with an amine compound represented by Chemical Formula 5 to prepare the compound represented by Chemical Formula 1c:

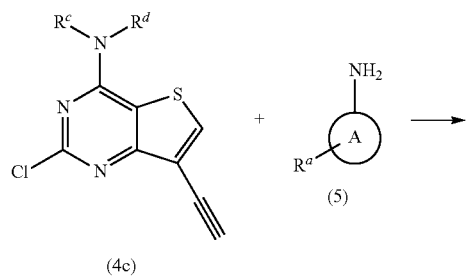

(wherein A, $R^a$, $R^c$ and $R^d$ are the same as defined in claim 1).

9. The preparation method according to claim 6, wherein the Suzuki coupling reaction or the Buchwald amination reaction is performed in the presence of a metal catalyst selected from $Pd_2(dba)_3$, $Pd(OAc)_2$, $PdCl_2(PPh_3)_2$ and $Pd(PPh_3)_4$.

10. The preparation method according to claim 7, wherein the Stille coupling reaction is performed in the presence of a metal catalyst selected from $Pd_2(dba)_3$, $Pd(OAc)_2$, $PdCl_2(PPh_3)_2$ and $Pd(PPh_3)_4$.

11. The preparation method according to claim 8, wherein the Sonogashira reaction is performed in the presence of a metal catalyst selected from $Pd_2(dba)_3$, $Pd(OAc)_2$, $PdCl_2(PPh_3)_2$ and $Pd(PPh_3)_4$.

12. The 2,4,7-substituted thieno[3,2-d]pyrimidine compound represented by Chemical Formula 1, wherein if the substituent B is alkenyl or alkynyl group, then Formula 1 is selected from the group consisting of Cis isomer of Formula 1, Trans isomer of Formula 1 or mixtures thereof.

* * * * *